United States Patent
Barten et al.

(10) Patent No.: US 12,274,205 B2
(45) Date of Patent: Apr. 15, 2025

(54) DELAYED HARVEST OF SHORT STATURE CORN PLANTS

(71) Applicant: MONSANTO TECHNOLOGY LLC, St. Louis, MO (US)

(72) Inventors: Ty J. Barten, Ankeny, IA (US); Bryce Lemke, Nevada, IA (US); Edward James Cargill, Chesterfield, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 17/298,979

(22) PCT Filed: Dec. 3, 2019

(86) PCT No.: PCT/US2019/064270
§ 371 (c)(1),
(2) Date: Jun. 2, 2021

(87) PCT Pub. No.: WO2020/117831
PCT Pub. Date: Jun. 11, 2020

(65) Prior Publication Data
US 2022/0039320 A1 Feb. 10, 2022

Related U.S. Application Data

(60) Provisional application No. 62/886,761, filed on Aug. 14, 2019, provisional application No. 62/778,368, filed on Dec. 12, 2018.

(51) Int. Cl.
| | |
|---|---|
| A01H 5/10 | (2018.01) |
| A01D 45/02 | (2006.01) |
| A01H 1/00 | (2006.01) |
| A01H 6/46 | (2018.01) |
| C12N 15/82 | (2006.01) |
| A01B 79/00 | (2006.01) |

(52) U.S. Cl.
CPC .............. *A01D 45/02* (2013.01); *A01H 1/121* (2021.01); *A01H 5/10* (2013.01); *A01H 6/4684* (2018.05); *C12N 15/82* (2013.01); *C12N 15/8262* (2013.01); *C12N 15/8297* (2013.01); *A01B 79/005* (2013.01)

(58) Field of Classification Search
None
See application file for complete search history.

(56) References Cited

U.S. PATENT DOCUMENTS

| | | |
|---|---|---|
| 4,368,592 A | 1/1983 | Welch |
| 5,159,135 A | 10/1992 | Umbeck |
| 5,188,958 A | 2/1993 | Moloney et al. |
| 5,322,938 A | 6/1994 | McPherson et al. |
| 5,352,605 A | 10/1994 | Fraley et al. |
| 5,463,174 A | 10/1995 | Moloney et al. |
| 5,510,474 A | 4/1996 | Quail et al. |
| 5,538,880 A | 7/1996 | Lundquist et al. |
| 5,550,318 A | 8/1996 | Adams et al. |
| 5,591,616 A | 1/1997 | Hiei et al. |
| 5,641,876 A | 6/1997 | McElroy et al. |
| 5,750,871 A | 5/1998 | Moloney et al. |
| 5,824,877 A | 10/1998 | Hinchee et al. |
| 5,850,019 A | 12/1998 | Maiti et al. |
| 5,939,539 A | 8/1999 | Lange et al. |
| 6,153,812 A | 11/2000 | Fry et al. |
| 6,160,208 A | 12/2000 | Lundquist et al. |
| 6,198,021 B1 | 3/2001 | Lange et al. |
| 6,372,211 B1 | 4/2002 | Isaac et al. |
| 6,380,467 B1 | 4/2002 | Duclos |
| 6,384,301 B1 | 5/2002 | Martinell et al. |
| 6,399,861 B1 | 6/2002 | Anderson et al. |
| 6,420,547 B1 | 7/2002 | Maiti et al. |
| 6,429,357 B1 | 8/2002 | McElroy et al. |
| 6,723,897 B2 | 4/2004 | Brown et al. |
| 6,765,133 B2 | 7/2004 | Koehring |
| 7,041,874 B2 * | 5/2006 | Johal ............... C07K 14/415 536/23.6 |
| 7,049,490 B2 | 5/2006 | Tanaka et al. |
| 7,057,088 B2 | 6/2006 | Tanaka et al. |
| 7,138,567 B2 | 11/2006 | Okawa et al. |
| 7,154,028 B2 | 12/2006 | Tanaka et al. |
| 7,597,055 B2 | 10/2009 | Choulet |
| 8,835,353 B2 | 9/2014 | Fugiel et al. |
| 8,843,283 B2 | 9/2014 | Strelioff et al. |
| 9,012,722 B2 | 4/2015 | Narva et al. |
| 9,040,774 B2 | 5/2015 | Ivashuta et al. |

(Continued)

FOREIGN PATENT DOCUMENTS

| | | |
|---|---|---|
| AU | 2016203359 B2 | 3/2018 |
| CN | 101440374 A | 5/2009 |

(Continued)

OTHER PUBLICATIONS

Spelhaug, A., "Predicting Your Corn Harvest Date", Peterson Farms Seed, Aug. 14, 2013.*

(Continued)

*Primary Examiner* — Phuong T Bui
(74) *Attorney, Agent, or Firm* — Dentons US LLP; David Lanzotti

(57) ABSTRACT

Methods for delayed harvesting of corn fields are provided herein. These methods provide an extended, flexible period of time to harvest corn. The methods allow growers to harvest their corn at the optimal time for drying down or accessing seed, without increasing the risk of losing yield to lodging.

38 Claims, 2 Drawing Sheets

(56) References Cited

U.S. PATENT DOCUMENTS

| | | | |
|---|---|---|---|
| 9,303,919 B2* | 4/2016 | Hultgren | F26B 3/347 |
| 9,309,512 B2 | 4/2016 | Allen et al. | |
| 9,845,479 B2 | 12/2017 | Beghyn et al. | |
| 10,123,473 B2 | 11/2018 | Cavender-Bares et al. | |
| 10,724,047 B2 | 7/2020 | Allen et al. | |
| 10,881,057 B2 | 1/2021 | Cannon et al. | |
| 11,627,736 B2 | 4/2023 | Barten et al. | |
| 11,632,921 B2 | 4/2023 | Cannon et al. | |
| 2002/0053095 A1 | 5/2002 | Brown et al. | |
| 2002/0162142 A1 | 10/2002 | Johal et al. | |
| 2003/0172409 A1* | 9/2003 | Horn | C12N 15/8205 |
| | | | 800/294 |
| 2003/0233679 A1 | 12/2003 | Brown et al. | |
| 2004/0053411 A1 | 3/2004 | Cullen et al. | |
| 2004/0121321 A1 | 6/2004 | Brown et al. | |
| 2004/0268441 A1 | 12/2004 | Vance et al. | |
| 2005/0037988 A1 | 2/2005 | Zamore et al. | |
| 2005/0064474 A1 | 3/2005 | Umov et al. | |
| 2005/0144669 A1 | 6/2005 | Reinhart et al. | |
| 2005/0197253 A1 | 9/2005 | Stoller et al. | |
| 2005/0251883 A1 | 11/2005 | Amasino et al. | |
| 2006/0200878 A1 | 9/2006 | Lutfiyya et al. | |
| 2006/0253933 A1 | 11/2006 | Brown et al. | |
| 2007/0174931 A1 | 7/2007 | Brown et al. | |
| 2007/0294789 A1 | 12/2007 | Ghiglione et al. | |
| 2008/0034453 A1 | 2/2008 | Cheikh et al. | |
| 2009/0031441 A1 | 1/2009 | Matsuoka et al. | |
| 2009/0070898 A1 | 3/2009 | Allen et al. | |
| 2009/0117617 A1 | 5/2009 | Holmes et al. | |
| 2009/0313725 A1 | 12/2009 | Yu et al. | |
| 2010/0095406 A1 | 4/2010 | Yu et al. | |
| 2010/0107283 A1 | 4/2010 | Dasgupta et al. | |
| 2011/0004958 A1 | 1/2011 | Aloni et al. | |
| 2011/0035839 A1 | 2/2011 | Lutfiyya et al. | |
| 2011/0126310 A1 | 5/2011 | Feng et al. | |
| 2011/0145940 A1 | 6/2011 | Voytas et al. | |
| 2011/0167517 A1 | 7/2011 | Danilevskaya et al. | |
| 2011/0185456 A1 | 7/2011 | Cheikh et al. | |
| 2011/0296555 A1 | 12/2011 | Ivashuta et al. | |
| 2011/0301073 A1 | 12/2011 | Gregory et al. | |
| 2012/0142062 A1 | 6/2012 | Doyon et al. | |
| 2012/0174260 A1 | 7/2012 | Narva et al. | |
| 2012/0216318 A1 | 8/2012 | La Rosa et al. | |
| 2012/0297501 A1 | 11/2012 | Beghyn et al. | |
| 2013/0117869 A1 | 5/2013 | Duchateau et al. | |
| 2013/0121101 A1 | 5/2013 | Ochampaugh et al. | |
| 2013/0260012 A1 | 10/2013 | Rommens et al. | |
| 2013/0283461 A1 | 10/2013 | Abad et al. | |
| 2013/0345937 A1 | 12/2013 | Strelioff et al. | |
| 2014/0013464 A1 | 1/2014 | Davie | |
| 2014/0074360 A1 | 3/2014 | Rosa et al. | |
| 2014/0165228 A1 | 6/2014 | Danilevskaya et al. | |
| 2014/0344996 A1 | 11/2014 | Inze et al. | |
| 2015/0052634 A1 | 2/2015 | Park et al. | |
| 2015/0201619 A1 | 7/2015 | Annigeri et al. | |
| 2015/0247154 A1 | 9/2015 | Ivashuta et al. | |
| 2015/0307889 A1 | 10/2015 | Petolino et al. | |
| 2015/0376641 A1 | 12/2015 | Etzioni et al. | |
| 2016/0010109 A1 | 1/2016 | Albertsen et al. | |
| 2016/0017349 A1 | 1/2016 | Ayele et al. | |
| 2016/0046956 A1 | 2/2016 | Yu et al. | |
| 2016/0050865 A1 | 2/2016 | Morse et al. | |
| 2016/0050920 A1 | 2/2016 | Ott et al. | |
| 2016/0076046 A1 | 3/2016 | Alexandrov et al. | |
| 2016/0319375 A1* | 11/2016 | Barten | A01H 1/04 |
| 2017/0079224 A1 | 3/2017 | Jolliffe et al. | |
| 2018/0051295 A1 | 2/2018 | Allen et al. | |
| 2019/0014730 A1 | 1/2019 | Dong et al. | |
| 2019/0014731 A1 | 1/2019 | Ovadya et al. | |
| 2019/0241903 A1 | 8/2019 | Ellis et al. | |
| 2019/0246586 A1 | 8/2019 | Cannon et al. | |
| 2019/0246619 A1 | 8/2019 | Barten et al. | |
| 2021/0032649 A1 | 2/2021 | Manjunath et al. | |
| 2022/0159905 A1 | 5/2022 | Barten et al. | |
| 2022/0159919 A1 | 5/2022 | Cannon et al. | |
| 2022/0162632 A1 | 5/2022 | Barten et al. | |
| 2022/0364108 A1 | 11/2022 | Allen et al. | |
| 2023/0110884 A1 | 4/2023 | Allen et al. | |
| 2023/0292733 A1 | 9/2023 | Barten et al. | |
| 2023/0323381 A1 | 10/2023 | Cannon et al. | |

FOREIGN PATENT DOCUMENTS

| | | |
|---|---|---|
| CN | 102149821 A | 8/2011 |
| CN | 102174519 A | 9/2011 |
| CN | 111778265 | 10/2020 |
| EP | 1398382 B1 | 11/2005 |
| JP | 3829157 B2 | 10/2006 |
| KR | 20150045611 A | 4/2015 |
| RU | 2013135491 A | 2/2015 |
| RU | 2013151447 A | 5/2015 |
| WO | WO 94/28141 A1 | 12/1994 |
| WO | WO 99/09174 A1 | 2/1999 |
| WO | WO 99/66029 A2 | 12/1999 |
| WO | WO 00/009722 A2 | 2/2000 |
| WO | WO 02/055725 A2 | 7/2002 |
| WO | WO 03/008540 A2 | 1/2003 |
| WO | 2004/092390 | 10/2004 |
| WO | WO 2006/032916 A2 | 3/2006 |
| WO | 2007/134234 | 11/2007 |
| WO | WO 2008/034648 A1 | 3/2008 |
| WO | WO 2010/002984 A1 | 1/2010 |
| WO | WO 2011/023537 A1 | 3/2011 |
| WO | WO 2013/037959 A1 | 3/2013 |
| WO | WO 2013/086499 A2 | 6/2013 |
| WO | WO 2014/055477 A2 | 4/2014 |
| WO | WO 2014/151749 A1 | 9/2014 |
| WO | WO 2015/168124 A1 | 11/2015 |
| WO | WO 2016/176286 A1 | 11/2016 |
| WO | WO 2017/011791 A1 | 1/2017 |
| WO | WO 2018/035354 A1 | 2/2018 |
| WO | WO 2018/119225 A1 | 6/2018 |
| WO | WO 2018/129302 A1 | 7/2018 |
| WO | WO 2019/161143 A1 | 8/2019 |
| WO | WO 2019/161145 A2 | 8/2019 |
| WO | WO 2019/161149 A1 | 8/2019 |

OTHER PUBLICATIONS

Elmore et al., "In-Field Drydown Rates and Harvest", Iowa State Unviersity Extension and Outreach, https://crops.extension.iastate.edu/cropnews/2010/09/field-drydown-rates-and-harvest, Sep. 28, 2010.*

International Search Report and Written Opinion mailed Apr. 22, 2020, in International Application No. PCT/US2019/064270, pp. 1-14.

"4 Series Sprayers," Published in May 2016, obtained from https://www[dot]deere[dot]com/en_CAF/docs/product/equipment/4_Series_Sprayers[dot]pdf (2016).

Amanullah et al., "Phenology, Growth, and Grain Yield of Maize as Influenced by Foliar Applied Urea at Different Growth Stages," Journal of Plant Nutrition 33:71-79 (2010).

"Corn Heibicide Application Timings," published by online by PennState Extension; obtained from https://extension[dot]psu[dot]edu/corn-herbicide-application-timings (2015).

Crommelinck et al., "Simulating an Autonomously Operating Low-Cost Static Terrestrial LiDAR for Multitemporal Maize Crop Height Measurements," Remote Sensing, 8(3):205, pp. 1-17 (2016).

D'Andrea et al., "Genotypic Variability in Morphological and Physiological Traits among Maize Inbred Lines-Nitrogen Responses," Crop Sci, 46:1266-1276 (2006).

GenBank Accession No. AY366085, "Zea mays cultivar B73 PGP1 (pgp1) gene, complete cds" (2003).

International Search Report and Written Opinion mailed Aug. 8, 2019, in International Application No. PCT/US2019/018129.

International Search Report and Written Opinion mailed May 10, 2019, in International Application No. PCT/US2019/018127.

Kempton, "Heritable Characters of Maize, III. Brachytic Culms," Jour. Hered., 11(1):111-115 (1920).

Lu, "Chapter 3 Research on Production Increase Technology in Late Harvesting of Maize in Optimum Period," Theory and Technology of Maize High Yield (2015).

(56) References Cited

OTHER PUBLICATIONS

Mourtzinis et al., "Corn Grain and Stover Yield Prediction at RI Growth Stage," Agronomy Journal, 105(4):1045-1050 (2013).
Multani et al., "Loss of an MDR Transporter in Compact Stalks of Maize br2 and Sorghum dw3 Mutants," Science, 302:81-84 (2003).
Pilu et al., "Isolation and characterization of a new mutant allele of brachytic 2 maize gene," Molecular Breeding, 20:83-91 (2007).
Qiao et al., "The influence of RNAi targeting of OsGA20ox2 gene on plant height in rice," Plant Molecular Biology Reporting 29.4:952-960 (2011).
Wang et al., "Analysis of hormone sensitivity of a dwarf mutant of maize," Journal of Northwest A&F University (Nat. Sci. Ed.) 45(8) (2017).
Weng et al., "Genome-Wide Association Study Identifies Candidate Genes That Affect Plant Height in Chinese Elite Maize (Zea mays L.) Inbred Lines," PLOS One 6(12) (2011).
Zaidi et al., "Phenotyping for Abiotic Stress Tolerance in Maize Heat Stress," CIMMYT, pp. 1-40 (2016).
Butzen, "Timing Corn Harvest," Crop Insights, (Sep. 2018).
Chen et al., "Identification and genetic mapping for rht-DM, a dominant dwarfing gene in mutant semi-dwarf maize using QTL-seq approach," Genes & Genomics 40, pp. 1091-1099 (Jun. 2018) (electronic publication).
Thomison et al., "Corn Response to Harvest Date a Affected by Plant Population and Hybrid," Agron J. 103, pp. 1765-1772 (Sep. 2011) (electronic publication).
Altschul, "Basic local alignment search tool." Journal of Molecular Biology, 15:403-410 (1990).
De Pater, et al., "The promoter of the rice gene GOS2 is active in various different monocot tissues and binds rice nuclear factor ASF-1," The Plant Journal, 2(6): 837-844 (1992).
Guo, et al., "RNA Silencing in Plants: Mechanism, Technologies and Applications in Horticulture Crops," Current Genomics, 17(6):476-489 (2016).
Hanway, "How a corn plant develops," Special Report No. 48, Iowa State University, CES, Ames, IA, (1966).
Inada, "Quality controls induced by aberrant translation," Nucleic Acids Research, 48(3): 1084-1096 (2020).
Israelsen, "Harvesting Corn Silage by Plant Moisture" article adapted from Crop and Soils Magazine, Utah State University Agricultural Extension Agents, (2009). Retrieved from <https://digitalcommons.usu.edu/cgi/viewcontent.cgi?article=1145&context=extension_curall>.
Karamyshev, et al., "Lost in Translation: Ribosome-Associated mRNA and Protein Quality Controls," Frontiers in Genetics, 9:431 (2018).
Last, et al., "pEmu: an improved promoter for gene expression in cereal cells," Theoretical and Applied Genetics, 81:581-588 (1991).
McElroy, et al., "Construction of expression vectors based on the rice actin 1 (Actl) 5' region for use in monocot transformation," Molecular and General Genetics MGG, 231: 150-160 (1991).
Nickless, et al., "Control of gene expression through the nonsense-mediated RNA decay pathway," Cell & Bioscience, 7:26 (2017).
Ritchie, S.W. et al., "How corn plants develops," Special Report No. 48, Iowa State University, CES, Ames, IA, Reprinted 1996.
Supplementary European Search Report dated Oct. 11, 2022 in EP 19 89 2688.
Szadeczky-Kardoss, et al., "The nonstop decay and the RNA silencing systems operate cooperatively in plants," Nucleic Acids Research, 46(9): 4632-4648 (2018).
Thompson, et al., "Clustal W: Improving the sensitivity of progressive multiple sequence alignment through sequence weighting, position-specific gap penalties and weight matrix choice," Nucleic Acids Research, 22: 4673-4680 (1994).
Wilson, et al., "Molecular Mechanisms of RNA Interference," Annual Review of Biophysics, 42: 217-39 (2013).
U.S. Appl. No. 18/176,206, filed Feb. 28, 2023, Barten et al.
U.S. Appl. No. 18/182,207, filed Mar. 10, 2023, Cannon et al.
Bage et al., Genetic characterization of novel and CRISPR-Cas9 gene edited maize brachytic 2 alleles, Plant Gene 21:100198, 2020.
Bolduc and Hake, The maize transcription factor KNOTTED1 directly regulates the gibberellin catabolismgene ga2ox1, Plant Cell 21:1647-1658, 2009.
R4038-sprayer by John Deere, available at https://kibbleeq.com/farmers/sprayers-&-applicators/self-propelled-sprayers/john-deere-sprayers/r4038-sprayer, accessed Apr. 29, 2024.
Sun et al., Identification and characterization of EI (Elongated Internode) gene in tomato (Solanum lycopersicum), Int. J. Mol. Sci. 20(2204):1-18, 2019.
Search Report dated Jul. 21, 2022, in Chinese Application 2017800639820 including English translation of related Office Action.
Allen, et al., "Evolution of microRNA genes by inverted duplication of target gene sequences in Arabidopsis thaliana," Nature Genetics, 36:1282-1290 (2004).
Allen, et al., "microRNA-directed phasing during Trans-acting siRNA Biogenesis in plants," Cell, 121(2):207-221 (2005).
Altschul, et al., "Basic Local Alignment Search Tool," Journal of Molecular Biology, 215(3):403-410 (1990).
Altschul, et al., "Gapped BLAST and PSI-BLAST: a new generation of protein database search programs," Nucleic Acids Research, 25 (17) : 3389-3402 (1997).
Ashikari, et al., "Loss-of-function of a Rice Gibberellin Biosynthetic Gene, GA20 oxidase (GA20ox-2), Led to the Rice 'Green Revolution'," Breeding Science, 52:143-150 (2002).
Axtell, et al., "A Two-Hit Trigger for siRNA Biogenesis in Plants," Cell, 127:565-577 (2006).
Beurdeley, et al., "Compact designer TALENs for efficient genome engineering", Nature Communications, 4: 1762 (2013).
Cai, et al., "Molecular Cloning, Characterization, and Expression Analysis of Genes Encoding Gibberellin 20-Oxidase in Dasypyrum villosum Dwarf Mutant," Plant Molecular Biology Reporter, 30:1110-1116 (2012).
Carrera, et al., "Changes in GA 20-oxidase gene expression strongly affect stem length, tuber induction and tuber yield of potato plants," The Plant Journal, 22(3):247-256 (2000).
Cermak, et al., "Efficient design and assembly of custom TALEN and other TAL effector-based constructs for DNA targeting," Nucleic Acids Research, 39(12):e82 (2011).
Chen, et al., "Identification and Functional Analysis of Flowering Related microRNAs in Common Wild Rice (Oryza rufipogon Griff.)," PLoS ONE, 8:e82844 (2013).
Chen, et al., "New insight in the Gibberellin biosynthesis and signal transduction," Plant Signaling & Behavior, 10(5):e1000140-1-e1000140-3:(2015).
Chen, et al., "The Maize DWARF1 Encodes a Gibberellin 3-Oxidase and is Dual Localized to the Nucleus and Cytosol," Plant Physiology, 166:2028-2039 (2014).
Chenna, et al., "Multiple sequence alignment with the Clustal series of programs," Nucleic Acids Research, 31(13):3497-3500 (2003).
Ciampitti, et al., "A comprehensive study of plant density consequences on nitrogen uptake dynamics of maize plants from vegetative to reproductive stages," Field Crops Research, 121(1):2-18 (2011).
Coles, et al., "Modification of gibberellin production and plant development in Arabidopsis by sense and antisense expression of gibberellin 20-oxidase genes," The Plant Journal, 17(5):547-556 (1999).
Davis, et al., "Gibberellin Biosynthesis in Maize. Metabolic Studies with $GA_{15}$, $GA_{24}$, $GA_{25}$, $GA_7$, and 2,3-Dehydro-$GA^{91}$," Plant Physiology, 121(3):1037-1045 (1999).
Doyle, et al., "TAL Effector-Nucleotide Targeter (TALE-NT) 2.0: tools for TAL effector design and target prediction," Nucleic Acids Research, 40:W117-122 (2012).
Du, et al., "Cloning and characterization of an up-regulated GA 20-oxidase gene in hybrid maize," Natural Science, 19(2):161-166 (2009).
Eriksson, et al., "GA4 is the Active Gibberellin in the Regulation of LEAFY Transcription and Arabidopsis Floral Initiation," The Plant Cell, 18(9):2172-2181 (2006).
Extended European Search Report dated Mar. 9, 2020, in European Patent Application No. 17842139.2.

(56) References Cited

OTHER PUBLICATIONS

Fagoaga, et al., "Engineering of gibberellin levels in citrus by sense and antisense overexpression of a *GA 20-oxidase* gene modifies plant architecture," Journal of Experimental Botany, 58(6):1407-1420 (2007).
Fambrini, et al., "The extreme dwarf phenotype of the GA-sensitive mutant of sunflower, dwarf2, is generated by a deletion in the *ent-kaurenoic acid oxidase1* (*HaKAO1*) gene sequence," Plant Molecular Biology, 75:431-450 (2011).
Franco-Zorrilla, et al., "Target mimicry provides a new mechanism for regulation of microRNA activity," Nature Genetics, 39: 1033-1037 (2007).
Gabsalilow, et al., "Site- and strand-specific nicking of DNA by fusion proteins derived from MutH and I-SceI or TALE repeats," Nucleic Acids Research, 41(7):e83 (2013).
Gaj, et al.. "ZFN, TALEN, and CRISPR/Cas-based methods for genome engineering," Trends Biotechnology, 31(7):397-405 (2013).
GenBank Accession No. AY105651.1, "*Zea mays* PC0130567 mRNA sequence," pp. 1-2, dated May 28, 2008.
GenBank Accession No. BT068785.2, "*Zea mays* full-length cDNA clone ZM_BFb0382B03 mRNA, complete cds," pp. 1-2, dated Jun. 15, 2012.
GenBank Accession No. EU963664.1, "*Zea mays* clone 265382 gibberellin 20 oxidase 2 mRNA, complete cds," pp. 1, dated Dec. 10, 2008.
Griffiths-Jones, et al., "Rfam: an RNA family database," Nucleic Acids Research, 31(1):439-441 (2003).
Gupta, et al., "Gibberellic acid in plant Still a mystery unresolved," Plant Signaling & Behavior, 8(9):e25504 (2013).
Han, et al., "Gibberellin-associated cisgenes modify growth, stature and wood properties in *Populus*," Plant Biotechnology Journal, 9(2):162-178 (2011).
Hedden, et al., "Gibberellin Biosynthesis: Enzymes, Genes and Their Regulation," Annu. Rev. Plant Physiol. Plant Mol. Biol., 48:431-60 (1997).
Hedden, "The genes of the Green Revolution," TRENDS in Genetics, 19(1):5-9 (2003).
Helliwell, et al "Constructs and Methods for Hairpin RNA-Mediated Gene Silencing in Plants," Methods in Enzymology, 392:24-35 (2003).
Huang, et al., "A Gibberellin-Mediated DELLA-NAC Signaling Cascade Regulates Cellulose Synthesis in Rice," The Plant Cell, 27(6):1681-1696 (2015).
Copenheaver. International Search Report and Written Opinion mailed Dec. 28, 2017, in International Application No. PCT/US2017/047405.
Jia, et al., "GA-20 oxidase as a candidate for the semidwarf gene *sdw1/denso* in barley," Functional & Integrative Genomics, 9:255-262 (2009).
Jia, et al., "Molecular characterization and functional analysis of barley semi-dwarf mutant Riso No. 9265," BMC Genomics, 16(927):1-11 (2015).
Jones-Rhoades, et al., "Computational Identification of Plant MicroRNAs and Their Targets, Including a Stress-Induced miRNA," Molecular Cell, 14(6):787-799 (2004).
Kamthan, et al., "Small RNAs in plants: recent development and application for crop improvement" Frontiers in Plant Science, 6:1-17 (2015).
Katoh, et al., "Specific residues at every third position of siRNA shape its efficient RNAi activity," Nucleic Acids Research, 35(4):e27 (2007).
Khvorova, et al., "Functional siRNAs and miRNAs Exhibit Strand Bias," Cell, 115(2):209-216 (2003).
Kim, "MicroRNA Biogenesis: Coordinated Cropping and Dicing," Nature Reviews Molecular Cell Biology, 6:376-385 (2005).
King, et al., "Selective Deactivation of Gibberellins below the Shoot Apex is Critical to Flowering but Not to Stem Elongation of *Lolium*," Molecular Plant, 1(2):295-307 (2008).

Kobayashi, et al., "Gibberellin Metabolism in Maize (The Stepwise Conversion of Gibberellin A12-Aldehyde to Gibberellin A20)," Plant Physiology, 110(2):413-418 (1996).
Kusaba, et al., "Isolation and expression analysis of gibberellin 20-oxidase homologous gene in apple," Journal of Experimental Botany, 52(335):375-376 (2001).
Lange, et al., "Gibberellin Biosynthesis and the Regulation of Plant Development," Plant Biology, 8(3):281-290 (2006).
Larkin, et al., "Clustal W and Clustal X version 2.0," Bioinformatics, 23(21):2947-48 (2007).
Liu, et al., "Analysis of Complementarity Requirements for Plant MicroRNA Targeting Using a *Nicotiana benthamiana* Quantitative Transient Assay," The Plant Cell, 26(2):741-753 (2014).
McElroy, et al., "Construction of expression vectors based on the rice actin 1 (Act1) 5' region for use in monocot transformation," Molecular and General Genetics MGG, 231:150-160 (1991).
Mitchum, et al., "Distinct and overlapping roles of two gibberellin 3-oxidases in *Arabidopsis* development," The Plant Journal, 45(5):804-818 (2006).
Molina, et al., "Transformation of a Dwarf *Arabidopsis* Mutant Illustrates Gibberellin Hormone Physiology and the Function of a Green Revolution Gene," Biochemistry and Molecular Biology Education, 37(3): 170-177 (2009).
Mutasa-Gottgens, et al., "Gibberellin as a factor in floral regulatory networks," Journal of Experimental Botany, 60(7):1979-1989 (2009).
Offtype—Definition of Offtype by Merriam-Webster, pp. 1, retrieved Sep. 18, 2023 <https://www.merriam-webster.com/dictionary/offtype>.
Oikawa, et al., "A role of OsGA20ox1, encoding an isoform of gibberellin 20-oxidase, for regulation of plant stature in rice," Plant Molecular Biology, 55:687-700 (2004).
Ookawa, et al., "Precise estimation of genomic regions controlling lodging resistance using a set of reciprocal chromosome segment substitution lines in rice," Scientific Reports, 6(30572) pp. 1-12 (2016).
Parizotto, et al., "In vivo investigation of the transcription, processing, endonucleolytic activity, and functional relevance of the spatial distribution of a plant miRNA, " Genes & Development, 18:2237-2242 (2004).
Pater, et al., "The promoter of the rice gene *GOS2* is active in various different monocot tissues and binds rice nuclear factor ASF-1," The Plant Journal, 2(6):837-844 (1992).
Peiffer, et al., "The Genetic Architecture of Maize Height," Genetics, 196(4):1337-1356 (2014).
Peng, et al., "'Green revolution' genes encode mutant gibberellin response modulators," Nature, 400:256-261 (1999).
Petti, et al., "Mapping of a Cellulose-Deficient Mutant Named *dwarf1-1* in *Sorghum bicolor* to the Green Revolution Gene *gibberellin20-oxidase* Reveals a Positive Regulatory Association between Gibberellin and Cellulose Biosynthesis," Plant Physiology, 169(1):705-716 (2015).
Plackett, et al., "Analysis of the Developmental Roles of the *Arabidopsis* Gibberellin 20-Oxidases Demonstrates That *GA20ox1*, -2, and -3 Are the Dominant Paralogs," The Plant Cell, 24(3):941-960 (2012).
Qiao, et al., "Alteration of rice growth and development via antisense expression of *OsGA20ox2* gene," African Journal of Biotechnology, 12(5):3898-3904 (2013).
Qiao, et al., "Modification of plant height via RNAi suppression of *OsGA20ox2* gene in rice," Euphytica, 158-35-45 (2007).
Qiao, et al., "The Influence of RNAi Targeting of *OsGA20ox2* Gene on Plant Height in Rice," Plant Molecular Biology Reporter, 29:952-960 (2011).
Reynolds, et al., "Rational siRNA design for RNA interference," Nature Biotechnology, 22(3):326-330 (2004).
Rhoades, et al., "Prediction of Plant MicroRNA Targets," Cell, 110(4):513-520 (2002).
Rieu, et al., "The gibberellin biosynthetic genes *AtGA20ox1* and *AtGA20ox2* act, partially redundantly, to promote growth and development throughout the *Arabidopsis* life cycle," The Plant Journal, 53 :488-504 (2008).
Ross, et al., "Gibberellin mutants," Physiologia Plantarum, 100(3):550-560 (1997).

(56) References Cited

OTHER PUBLICATIONS

Sarkar, et al., "Relationship between gibberellins, height, and stress tolerance in barley (*Hordeum vulgare* L.) seedlings," Plant Growth Regulation, 42:125-135 (2004).
Sasaki, et al., "A mutant gibberellin-synthesis gene in rice," Nature, 416:701-702 (2002).
Gromova, Search Report dated Jun. 24, 2021, in Russian Patent Application 2019105536, and English translation of the same (pp. 1-4).
Singh, "The green revolution and the evolution of agricultural education and research in India," Genome, 42(4):557-561 (1999).
Song, et al., "Association of the molecular regulation of ear leaf senescence/stress response and photosynthesis/metabolism with heterosis at the reproductive stage in maize," Scientific Reports, 6: 29843 (2016).
Song, et al., "Flowering time regulation: photoperiod- and temperature-sensing in leaves," Trends in Plant Science, 18(10):575-583 (2013).
Song, et al., "Genome-wide identification of gibberellins metabolic enzyme genes and expression profiling analysis during seed germination in maize," Gene, 482(1-2):34-42 (2011).
Spielmeyer, et al., "Semidwarf (sd-1), "green revolution" rice, contains a defective gibberellin 20-oxidase gene," PNAS, 99(13):9043-9048 (2002).
Sun, "Gibberellin Metabolism, Perception and Signaling Pathways in *Arabidopsis*," The *Arabidopsis* Book, 2008(6): pp. 1-28 (2008).
Sunkar, et al., "Novel and Stress-Regulated MicroRNAs and Other Small RNAs from *Arabidopsis*," Plant Cell, 16(8):2001-2019 (2004).
Obel. Supplementary Partial European Search Report dated Jan. 14, 2020, in European Patent Application No. 17842139.2.
Svitashev, et al., "Targeted Mutagenesis, Precise Gene Editing, and Site-Specific Gene Insertion in Maize Using Cas9 and Guide RNA," Plant Physiology, 169(2):931-945 (2015).
Teng, et al., "*ZmGA3ox2*, a candidate gene for a major QTL, *qPH3.1*, for plant height in maize," The Plant Journal, 73(3):405-416 (2013).
Thompson, et al., "CLUSTAL W: improving the sensitivity of progressive multiple sequence alignment through sequence weighting, position-specific gap penalties and weight matrix choice," Nucleic Acids Research, 22(22):4673-4680 (1994).
Tollenaar, et al., "Effect of Defoliation on Kernel Development in Maize," Canadian Journal of Plant Science, 58(1):207-212 (1978).
Tong, et al., "Reply: Brassinosteroid Regulates Gibberellin Synthesis to Promote Cell Elongation in Rice: Critical Comments on Ross and Quittenden's Letter," The Plant Cell, vol. 28, pp. 833-835, (2016).
Traore, et al., "Bt and Non-Bt Maize Growth and Development as Affected by Temperature and Drought Stress," Agronomy Journal, 92(5): 1027-1035 (2000).
Unterholzner, et al., "Reply: Interaction Between Brassinosteroids and Gibberellins: Synthesis or Signaling? In *Arabidopsis* Both!," The Plant Cell, vol. 28, pp. 836-839, (2016).
Urakami, et al., "Immunomodulation of gibberellin biosynthesis using an anti-precursor gibberellin antibody confers gibberellin-deficient phenotypes," Planta, 228:863-873 (2008).
Voytas, "Plant Genome Engineering with Sequence-Specific Nucleases," Annual Review of Plant Biology, 64:327-50 (2013).
Wang, et al., "Gibberellin Biosynthetic Deficiency is Responsible for Maize Dominant Dwarf11 (*D11*) Mutant Phenotype: Physiological and Transcriptomic Evidence," PLoS One, 8(6):e66466:1-8 (2013).
Wang, et al., "More than meets the eye? Factors that affect target selection by plant miRNAs and heterochromatic siRNAs," Current Opinion Plant Biology, 27:118-124 (2015).
Weng, et al., "Genome-Wide Association Study Identifies Candidate Genes That Affect Plant Height in Chinese Elite Maize (*Zea mays* L.) Inbred Lines," PLoS One, 6(12):e29229 pp. 1-8 (2011).
Wu, et al., "Target specificity of the CRISPR-Cas9 system," Quantitative Biology, 2(2):59-70 (2014).
Xiao, et al., "Dissection of GA 20-oxidase members affecting tomato morphology by RNAi-mediated silencing," Plant Growth Regulation, 50:179-189 (2006).
Yamaguchi, et al., "Gibberellin Acts Positively Then Negatively to Control Onset of Flower Formation in *Arabidopsis*," Science, 344(6184):638-641 (2014).
Yamaguchi, "Gibberellin Metabolism and its Regulation," Annual Review of Plant Biology, 59:225-251 (2008).
Yanik, et al., "TALE-PvuII Fusion Proteins—Novel Tools for Gene Targeting," PLoS One, 8(12):e82539 pp. 1-13 (2013).
Yin, et al., "In-Season Prediction of Corn Yield Using Plant Height under Major Production Systems," Agronomy Journal, 103(3):923-929 (2011).
Yoshikawa, et al., "A pathway for the biogenesis of trans-acting siRNAs in *Arabidopsis*," Genes & Development, 19:2164-2175 (2005).
Zeng, et al., "Both Natural and Designed Micro RNAs Can Inhibit the Expression of Cognate mRNAs When Expressed in Human Cells," Molecular Cell, 9(6): 1327-1333 (2002).
Rodriquez. Invitation to Pay Additional Fees for Application No. PCT/US23/62985, mailed May 23, 2023.
Rodriquez. International Search Report and Written Opinion for Application No. PCT/US23/62985, mailed Jul. 27, 2023.
Hill and Furrow, "Pinch or Push Your Corn: Scouting for Lodging Potential", University of Illinois Urbana-Champaign, Illinois Extension, Sep. 12, 2016, 2 pages.
Xia et al., "A book to understand high corn yield and disaster prevention and reduction technology", China Farmers Press, May 2016, p. 135.
Zhang. Chinese Office Action regarding Chinese Patent Application No. 201980025083.0, dated Dec. 1, 2023, 19 pages.
Chen, et al. "Development of dwarfish and yield-effective GM maize through passivation of bioactive gibberellin." Transgenic Res, 28:589-599, (2019).
Kollner, et al. "Herbivore-Induced Sabath Methyltransferases of Maize that Methylate Anthranilic Acid Using S-Adenosyl-L-Methionine." Plant Physiology, vol. 153, pp. 1795-1807, (2010).
Zhang, et al. "Maize brachtic2 (br2) suppresses the elongation of lower internodes for excessive auxin accumulation in the intercalary meristem region." BMC Plant Biology, 19:589, (2019).
Sehgal. "Inbred-Hybrod Method of Maize Improvement." Proceeding of the Caribbean Food Crops Society Fourth Annual Meeting, 1966.

\* cited by examiner

DELAYED HARVEST OF SHORT STATURE
CORN PLANTS

CROSS-REFERENCE TO RELATED
APPLICATIONS

This application is a U.S. National Stage of International Application No. PCT/US2019/064270, filed Dec. 3, 2019, which claims the benefit of U.S. Provisional Application No. 62/886,761, filed Aug. 14, 2019, and U.S. Provisional Application No. 62/775,368, filed Dec. 4, 2018, all of which are incorporated by reference in their entireties herein.

FIELD OF THE INVENTION

The present disclosure relates to methods of delayed harvest of corn fields.

BACKGROUND

Corn can be harvested after fertilization, grain fill and maturity, but typically after drying down to a desired moisture content for storage. Growers have to balance product value, plant health, kernel moisture content, and standability (e.g., due to the propensity of corn to lodge) of corn plants when determining the optimum time for harvesting. If a grower harvests corn before it reaches its optimal kernel moisture content, the grower may have to use artificial drying methods to further reduce the kernel moisture content before storage. Conversely, if a grower waits to harvest corn (or cannot harvest due to physical weather barriers such as rain or snow) until it reaches or passes optimal kernel moisture, then the longer the amount of time the crop remains in the field, the greater the risk of lodging from weather events (e.g., strong winds) and/or plant senescence (i.e., deterioration from age). Thus, there is a need for farmers to have greater flexibility to leave corn plants in the field for later harvest to allow for greater access and/or dry down of kernels.

SUMMARY

In an aspect, this disclosure provides a method comprising harvesting a plurality of corn plants from a field at least 50 days after fertilization or silking of at least 50% of said plurality of corn plants, wherein fewer than or equal to 50% of said corn plants have lodged at the time of harvest.

In an aspect, this disclosure provides a method comprising harvesting a plurality of corn plants from a field at least 50 days after at least 50% of said corn plants have reached R3 stage, wherein fewer than or equal to 50% of said corn plants have lodged at the time of harvest.

In an aspect, this disclosure provides a method comprising harvesting a plurality of corn plants from a field at least 50 days after fertilization or silking of at least 50% of said plurality of corn plants, wherein the average kernel moisture content is less than or equal to 30% or the kernel moisture content of a corn plant of the plurality of corn plants is less than or equal to 30%, and wherein fewer than or equal to 50% of said corn plants have lodged at the time of harvest.

In an aspect, this disclosure provides a method comprising harvesting a plurality of corn plants from a field at least 50 days after at least 50% of said corn plants have reached R3 stage, wherein average kernel moisture content is less than or equal to 30% or the kernel moisture content of a corn plant of the plurality of corn plants is less than or equal to 30%, and wherein fewer than or equal to 50% of said corn plants have lodged at the time of harvest.

In an aspect, this disclosure provides a method comprising harvesting a plurality of corn plants from a field at least 50 days after at fertilization or silking of at least 50% of said plurality of corn plants, wherein the average yield of said field is at least 170 bushels per acre, and wherein fewer than or equal to 50% of said corn plants have lodged at the time of harvest.

In an aspect, this disclosure provides a method comprising harvesting a plurality of corn plants from a field at least 50 days after at least 50% of said corn plants have reached R3 stage, wherein the average yield of said field is at least 170 bushels per acre, and wherein fewer than or equal to 50% of said corn plants have lodged at the time of harvest.

In an aspect, this disclosure provides a method comprising harvesting a plurality of corn plants from a field at least 1 day after the average kernel moisture content of at least 50% of said plurality of corn plants is between 10% and 30%, or after the kernel moisture content of a corn plant of the plurality of corn plants is between 10% and 30%, wherein fewer than or equal to 50% of said corn plants have lodged at the time of harvest.

DETAILED DESCRIPTION

Figure 1:
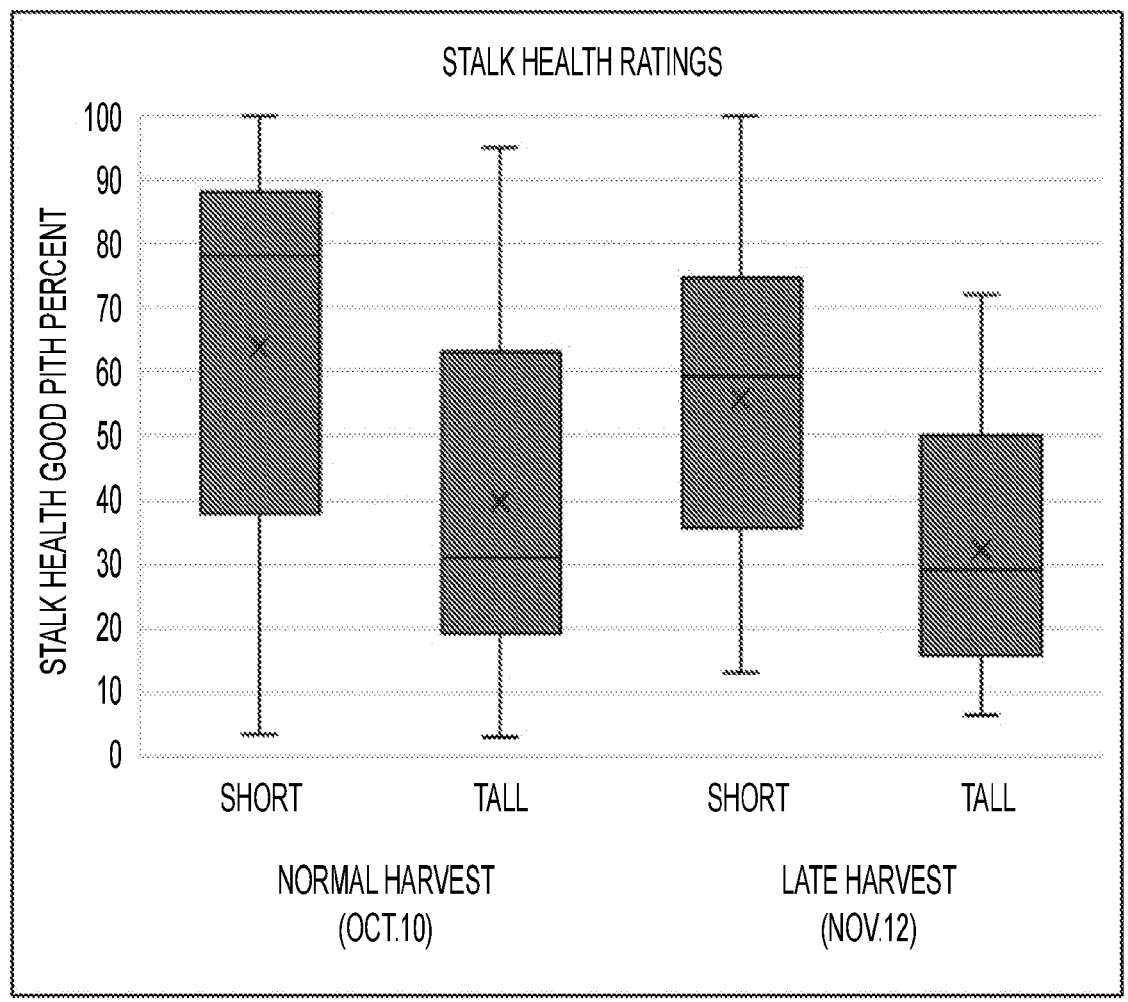
FIG. 1 depicts the stalk health ratings of short and tall corn plants at normal and late harvest times.

Unless defined otherwise, all technical and scientific terms used have the same meaning as commonly understood by one of ordinary skill in the art to which this disclosure belongs. Unless otherwise provided, where a term is provided in the singular, this disclosure also contemplates the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A, C, and D; A, B, and C; A and C; B and C; A and B; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

As well understood in the art, metric measurement values provided herein can be easily converted to standard (S.I.) units where relevant, and vice versa.

As used herein, a "plant" includes an explant, plant part, seedling, plantlet or whole plant at any stage of regeneration or development. As commonly understood, a "corn plant" or "maize plant" refers to any plant of species *Zea mays* and includes all plant varieties that can be bred with corn, including wild maize species.

As used herein, the term "plurality" in reference to an item means two or more of such items. For example, a "plurality of plants" means two or more plants.

In an aspect, corn plants disclosed herein are selected from the subspecies *Zea mays* L. ssp. *mays*. In an additional aspect, corn plants disclosed herein are selected from the group *Zea mays* L. subsp. *mays indentata*, otherwise known as dent corn. In another aspect, corn plants disclosed herein are selected from the group *Zea mays* L. subsp. *mays indurata*, otherwise known as flint corn. In an aspect, corn plants disclosed herein are selected from the group *Zea mays* L. subsp. *mays Saccharata*, otherwise known as sweet corn. In another aspect, corn plants disclosed herein are selected from the group *Zea mays* L. subsp. *mays amylacea*, otherwise known as flour corn. In a further aspect, corn plants disclosed herein are selected from the group *Zea mays* L. subsp. *mays everta*, otherwise known as popcorn. Plants disclosed herein also include hybrids, inbreds, partial inbreds, or members of defined or undefined populations.

Growers must balance crop prices, standability, plant health, and kernel moisture content when determining when to harvest a corn field. As provided herein, corn plants with better standability, such as dwarf corn plants, semi-dwarf corn plants, and brachytic corn plants, are resistant to lodging and thus can remain in the field for a longer period of time prior to harvest without significant loss of yield, or with improved yield relative to taller corn plants (especially when compared to corn plants that have lodged). According to aspects of the present disclosure, the improved standability of short stature corn plants provides growers and seed producers with more flexibility on when to harvest, allows more time for drying down seed or grain prior to harvest, and/or enables or improves direct harvest applications, particularly in corn seed production operations. As used herein, "direct harvesting" refers to the harvesting of crop seeds from plants with a combine harvester in the field with little or no further drying or other processing or desiccation steps prior to seed storage. As used herein, "standability" refers to the ability of a plant or a plurality, population or field of plants, such as a corn plant or a plurality, population or field of corn plants, to stand upright in a position that enables the plant(s) to be harvested by standard farm equipment (e.g., a combine harvester). As used herein, "lodging" can refer to either "stalk lodging" or "root lodging." Stalk lodging occurs when the corn plant stalk is severely bent or broken below the ear. Root lodging occurs when the corn plant is leaning at an angle (e.g., greater than or equal to 45° relative to perpendicular from the ground, or at an angle less than 45° relative to the ground). Lodged corn plants, whether stalk lodged and/or root lodged, severely limit harvestability by standard farm equipment (e.g., a combine harvester) resulting in up to 100% yield loss of the lodged corn plants.

Growers will leave harvestable corn standing in a field to reduce the kernel moisture content of the grain. Optimal kernel moisture content can vary by growing region and by individual grower. Typically, kernel moisture content decreases the longer the corn plants are left in the field (e.g., the longer the period of time between fertilization or reaching maturity and harvest). However, extending the period of time between fertilization (or reaching maturity or some other developmental stage) and harvesting can increase the chance that plants will lodge, which can result in significant decreases in yield (even up to 100%). As provided herein, by providing plants with reduced heights that have high standability performance (i.e., resistance to lodging), growers are enabled to allow for greater periods of time until harvest without increasing (or significantly or substantially increasing) their risk of yield loss due to lodging. Typical grain moisture contents for harvesting corn are between 15% and 25%, although wider ranges of 13-30% or higher are possible. According to present embodiments, corn plants may be left in the field for a longer period of time after reaching a given grain moisture content percentage.

In an aspect, a method provided herein comprises harvesting a plurality of corn plants from a field at least 30 days, at least 40 days, at least 50 days, at least 60 days, at least 70 days, at least 80 days, at least 90 days, at least 100 days, or at least 110 days after at least 50%, at least 60%, at least 70%, at least 80%, at least 90% or 100% of said corn plants have reached R3 stage, wherein fewer than or equal to 50% of said corn plants have lodged at the time of harvest. In another aspect, a method comprises harvesting a plurality of corn plants from a field at least 30 days, at least 40 days, at least 50 days, at least 60 days, at least 70 days, at least 80 days, at least 90 days, at least 100 days, or at least 110 days after at least 50%, at least 60%, at least 70%, at least 80%, at least 90% or 100% of said corn plants have reached R3 stage, wherein average kernel moisture content is less than or equal to 30% or the kernel moisture content of a corn plant of the plurality of corn plants is less than or equal to 30%, and wherein fewer than or equal to 50% of said corn plants have lodged at the time of harvest. In another aspect, a method comprising harvesting a plurality of corn plants from a field at least 30 days, at least 40 days, at least 50 days, at least 60 days, at least 70 days, at least 80 days, at least 90 days, at least 100 days, or at least 110 days after at least 50%, at least 60%, at least 70%, at least 80%, at least 90% or 100% of said corn plants have reached R3 stage, wherein the average yield of said field is at least 170 bushels per acre, and wherein fewer than or equal to 50% of said corn plants have lodged at the time of harvest.

In an aspect, a method provided herein comprises harvesting a plurality of corn plants from a field at least 30 days, at least 40 days, at least 50 days, at least 60 days, at least 70 days, at least 80 days at least 90 days, at least 100 days, or at least 110 days after fertilization or silking of said plurality of corn plants, wherein fewer than or equal to 50% of said corn plants have lodged at the time of harvest. In another aspect, a method provided herein comprises harvesting a plurality of corn plants from a field at least 30 days, at least 40 days, at least 50 days, at least 60 days, at least 70 days, at least 80 days at least 90 days, at least 100 days, or at least 110 days after fertilization or silking of said plurality of corn plants, wherein the average kernel moisture content is less than or equal to 30% or the kernel moisture content of a corn plant of the plurality of corn plants is less than or equal to 30%, and wherein fewer than or equal to 50% of said corn plants have lodged at the time of harvest. In another aspect, a method provided herein comprises harvesting a plurality of corn plants from a field at least 30 days, at least 40 days, at least 50 days, at least 60 days, at least 70 days, at least 80 days at least 90 days, at least 100 days, or at least 110 days after at fertilization or silking of said plurality of corn plants, wherein the average yield of said field is at least 170 bushels per acre, and wherein fewer than or equal to 50% of said corn plants have lodged at the time of harvest.

In an aspect, a method provided herein comprises harvesting a plurality of corn plants from a field when, or at least 1 day after, the average kernel moisture content of said plurality of corn plants is between 10% and 30%, or less than or equal to 30%, or the kernel moisture content of a corn plant of the plurality of corn plants is between 10% and 30%, or less than or equal to 30%, wherein fewer than or equal to 50% of said corn plants have lodged at the time of harvest. In an aspect, methods provided herein comprise harvesting a plurality of corn plants from a field when, or at least 1 day after, the average kernel moisture content of said plurality of corn plants is between 15% and 25%, or less than or equal to 25%, or less than or equal to 20%, or less than or equal to 15%, or the kernel moisture content of a corn plant of the plurality of corn plants is between 15% and 25%, or less than or equal to 25%, or less than or equal to 20%, or less than or equal to 15%, wherein fewer than or equal to 50% of said corn plants have lodged at the time of harvest. In each of these aspects, the average yield of said plants in a field may be at least 170 bushels per acre.

In an aspect, a method provided herein comprises harvesting a plurality of corn plants from a field at least 30 days, at least 40 days, at least 50 days, at least 60 days, at least 70 days, at least 80 days, at least 90 days, at least 100 days, or at least 110 days after fertilization or silking of at least 50%, at least 60%, at least 70%, at least 80%, at least 85%, at least 90%, or 100% of said plurality of corn plants, wherein fewer than or equal to 50% of said corn plants have lodged at the time of harvest. In another aspect, a method provided herein comprises harvesting a plurality of corn plants from a field at least 30 days, at least 40 days, at least 50 days, at least 60 days, at least 70 days, at least 80 days, at least 90 days, at least 100 days, or at least 110 days after fertilization or silking of at least 50%, at least 60%, at least 70%, at least 80%, at least 85%, at least 90%, or 100% of said plurality of corn plants, wherein the average kernel moisture content is less than or equal to 30% or the kernel moisture content of a corn plant of the plurality of corn plants is less than or equal to 30%, and wherein fewer than or equal to 50% of said corn plants have lodged at the time of harvest. In another aspect, a method provided herein comprises harvesting a plurality of corn plants from a field at least 30 days, at least 40 days, at least 50 days, at least 60 days, at least 70 days, at least 80 days, at least 90 days, at least 100 days, or at least 110 days after at fertilization or silking of at least 50%, at least 60%, at least 70%, at least 80%, at least 85%, at least 90%, or 100% of said plurality of corn plants, wherein the average yield of said field is at least 170 bushels per acre, and wherein fewer than or equal to 50% of said corn plants have lodged at the time of harvest.

In an aspect, a method provided herein comprises harvesting a plurality of corn plants from a field when, or at least 1 day after, the average kernel moisture content of at least 50%, at least 60%, at least 70%, at least 80%, at least 85%, at least 90%, or 100% of said plurality of corn plants is between 10% and 30%, or less than or equal to 30%, or the kernel moisture content of a corn plant of the plurality of corn plants is between 10% and 30%, or less than or equal to 30%, wherein fewer than or equal to 50% of said corn plants have lodged at the time of harvest. In an aspect, methods provided herein comprise harvesting a plurality of corn plants from a field when, or at least 1 day after, the average kernel moisture content of at least 50%, at least 60%, at least 70%, at least 80%, at least 85%, at least 90%, or 100% of said plurality of corn plants is between 15% and 25%, or less than or equal to 25%, or less than or equal to 20%, or less than or equal to 15%, or the kernel moisture content of a corn plant of the plurality of corn plants is between 15% and 25%, or less than or equal to 25%, or less than or equal to 20%, or less than or equal to 15%, wherein fewer than or equal to 50% of said corn plants have lodged at the time of harvest. In each of these aspects, the average yield of said plants in a field may be at least 170 bushels per acre.

In an aspect, a method provided herein further comprises growing a plurality of corn plants in a corn field prior to harvesting the plurality of corn plants.

In an aspect, corn plants provided herein are inbred corn plants. As used herein, the term "inbred" means a line that has been bred for genetic homogeneity. In another aspect, corn plants provided herein are hybrid corn plants. As used herein, the term "hybrid" means a progeny of mating between at least two genetically dissimilar parents or inbreds. In an aspect, corn plants provided herein are transgenic, mutant and/or edited corn plants.

In an aspect, at least 10% of the corn plants in a field are inbred corn plants. In an aspect, at least 20% of the corn plants in a field are inbred corn plants. In an aspect, at least 30% of the corn plants in a field are inbred corn plants. In an aspect, at least 40% of the corn plants in a field are inbred corn plants. In an aspect, at least 50% of the corn plants in a field are inbred corn plants. In an aspect, at least 60% of the corn plants in a field are inbred corn plants. In an aspect, at least 70% of the corn plants in a field are inbred corn plants. In an aspect, at least 80% of the corn plants in a field are inbred corn plants. In an aspect, at least 90% of the corn plants in a field are inbred corn plants. In an aspect, 100% of the corn plants in a field are inbred corn plants.

In an aspect, between 1% and 100% of the corn plants in a field are inbred corn plants. In an aspect, between 10% and 100% of the corn plants in a field are inbred corn plants. In an aspect, between 20% and 100% of the corn plants in a field are inbred corn plants. In an aspect, between 30% and 100% of the corn plants in a field are inbred corn plants. In an aspect, between 40% and 100% of the corn plants in a field are inbred corn plants. In an aspect, between 50% and 100% of the corn plants in a field are inbred corn plants. In an aspect, between 60% and 100% of the corn plants in a field are inbred corn plants. In an aspect, between 70% and 100% of the corn plants in a field are inbred corn plants. In an aspect, between 80% and 100% of the corn plants in a field are inbred corn plants. In an aspect, between 90% and 100% of the corn plants in a field are inbred corn plants.

In an aspect, at least 10% of the corn plants in a field are hybrid corn plants. In an aspect, at least 20% of the corn plants in a field are hybrid corn plants. In an aspect, at least 30% of the corn plants in a field are hybrid corn plants. In an aspect, at least 40% of the corn plants in a field are hybrid corn plants. In an aspect, at least 50% of the corn plants in a field are hybrid corn plants. In an aspect, at least 60% of the corn plants in a field are hybrid corn plants. In an aspect, at least 70% of the corn plants in a field are hybrid corn plants. In an aspect, at least 80% of the corn plants in a field are hybrid corn plants. In an aspect, at least 90% of the corn plants in a field are hybrid corn plants. In an aspect, 100% of the corn plants in a field are hybrid corn plants.

In an aspect, between 1% and 100% of the corn plants in a field are hybrid corn plants. In an aspect, between 10% and 100% of the corn plants in a field are hybrid corn plants. In an aspect, between 20% and 100% of the corn plants in a field are hybrid corn plants. In an aspect, between 30% and 100% of the corn plants in a field are hybrid corn plants. In an aspect, between 40% and 100% of the corn plants in a field are hybrid corn plants. In an aspect, between 50% and 100% of the corn plants in a field are hybrid corn plants. In an aspect, between 60% and 100% of the corn plants in a field are hybrid corn plants. In an aspect, between 70% and 100% of the corn plants in a field are hybrid corn plants. In an aspect, between 80% and 100% of the corn plants in a field are hybrid corn plants. In an aspect, between 90% and 100% of the corn plants in a field are hybrid corn plants.

In another aspect, a corn plant provided herein is a semi-dwarf corn plant. As used herein, a "semi-dwarf plant" refers to a plant having a stature or height that is reduced relative to a control wild-type plant by at least 5%, at least 10%, at least 15%, at least 20%, at least 25%, at least 30%, at least 35%, at least 40%, at least 45%, or at least 50%. Such a semi-dwarf plant can be characterized by a reduced stem, stalk, or trunk length when compared to the control wild-type plant under comparable growth conditions, which can result from fewer internodes or shorter average internode length. As used herein, an "internode" refers to the region between two nodes on a corn stalk, and a "node" refers to the point on the corn stalk (e.g., stem) where leaves and/or ears originate.

In an aspect, at least 10% of the corn plants in a field are semi-dwarf corn plants. In an aspect, at least 20% of the corn plants in a field are semi-dwarf corn plants. In an aspect, at least 30% of the corn plants in a field are semi-dwarf corn plants. In an aspect, at least 40% of the corn plants in a field are semi-dwarf corn plants. In an aspect, at least 50% of the corn plants in a field are semi-dwarf corn plants. In an aspect, at least 60% of the corn plants in a field are semi-dwarf corn plants. In an aspect, at least 70% of the corn plants in a field are semi-dwarf corn plants. In an aspect, at least 80% of the corn plants in a field are semi-dwarf corn plants. In an aspect, at least 90% of the corn plants in a field are semi-dwarf corn plants. In an aspect, 100% of the corn plants in a field are semi-dwarf corn plants.

In an aspect, between 1% and 100% of the corn plants in a field are semi-dwarf corn plants. In an aspect, between 10% and 100% of the corn plants in a field are semi-dwarf corn plants. In an aspect, between 20% and 100% of the corn plants in a field are semi-dwarf corn plants. In an aspect, between 30% and 100% of the corn plants in a field are semi-dwarf corn plants. In an aspect, between 40% and 100% of the corn plants in a field are semi-dwarf corn plants. In an aspect, between 50% and 100% of the corn plants in a field are semi-dwarf corn plants. In an aspect, between 60% and 100% of the corn plants in a field are semi-dwarf corn plants. In an aspect, between 70% and 100% of the corn plants in a field are semi-dwarf corn plants. In an aspect, between 80% and 100% of the corn plants in a field are semi-dwarf corn plants. In an aspect, between 90% and 100% of the corn plants in a field are semi-dwarf corn plants.

In an aspect, a corn plant provided herein is a dwarf corn plant. As used herein, a "dwarf" plant refers to an atypically small plant. Generally, such a "dwarf plant" has a stature or height that is reduced from that of a control wild-type plant (e.g., a sibling plant comprising all other traits except the dwarf trait) by at least 30%, at least 35%, at least 40%, at least 45%, at least 50%, at least 55%, at least 60%, or at least 75%.

In an aspect, at least 10% of the corn plants in a field are dwarf corn plants. In an aspect, at least 20% of the corn plants in a field are dwarf corn plants. In an aspect, at least 30% of the corn plants in a field are dwarf corn plants. In an aspect, at least 40% of the corn plants in a field are dwarf corn plants. In an aspect, at least 50% of the corn plants in a field are dwarf corn plants. In an aspect, at least 60% of the corn plants in a field are dwarf corn plants. In an aspect, at least 70% of the corn plants in a field are dwarf corn plants. In an aspect, at least 80% of the corn plants in a field are dwarf corn plants. In an aspect, at least 90% of the corn plants in a field are dwarf corn plants. In an aspect, 100% of the corn plants in a field are dwarf corn plants.

In an aspect, between 1% and 100% of the corn plants in a field are dwarf corn plants. In an aspect, between 10% and 100% of the corn plants in a field are dwarf corn plants. In an aspect, between 20% and 100% of the corn plants in a field are dwarf corn plants. In an aspect, between 30% and 100% of the corn plants in a field are dwarf corn plants. In an aspect, between 40% and 100% of the corn plants in a field are dwarf corn plants. In an aspect, between 50% and 100% of the corn plants in a field are dwarf corn plants. In an aspect, between 60% and 100% of the corn plants in a field are dwarf corn plants. In an aspect, between 70% and 100% of the corn plants in a field are dwarf corn plants. In an aspect, between 80% and 100% of the corn plants in a field are dwarf corn plants. In an aspect, between 90% and 100% of the corn plants in a field are dwarf corn plants.

There are different ways in which a corn plant can be made to have a shorter semi-dwarf plant height. According to many aspects, a corn plant can be made shorter or semi-dwarf relative to a control plant by lowering the level(s) of active GAs in one or more tissue(s) of the plant, such as by suppressing, mutating or editing a GA oxidase gene in the corn plant. In an aspect, a corn plant provided herein comprises a recombinant polynucleotide capable of suppressing expression of one or more GA20 oxidase and/or GA3 oxidase gene(s) and/or mRNA(s) transcribed therefrom. Alternatively, a corn plant provided herein comprises one or more mutation(s) or edit(s) in one or more GA20 oxidase and/or GA3 oxidase gene(s). According to other aspects, corn plants can have a mutation or edit in an auxin, brassinosteroid, jasmonic acid, cell cycle regulation, and/or other pathway gene(s) that are shown to affect plant height. According to yet further embodiments, corn plants can be made shorter by application of one or more chemistries shown to affect plant height. According to another aspect, a corn plant or plurality of corn plants provided herein can comprise a mutation or edit in one or more loci or genes, or a transgene targeting such one or more loci or genes, that have been associated with a short stature phenotype in corn, such as one or more of the following: anther ear 1 (An1), brachytic 1 (Br1), *brevis* plant 1 (Bv1) or brachytic 3 (br3), crinkly 4 (Cr4), compact plant 2 (Ct2), dwarf plant 1 (d1), dwarf plant 8 (d8), dwarf plant 9 (d9), nana plant 1 (Na1), nana plant 2 (Na2), non-chromosomal stripe 3 (Nsc3), narrow leaf dwarf 1 (N1d1), reduced plant 1 (Rd1), semi-dwarf 1 (Sdw1), semi-dwarf 2 (Sdw2), tangled 1 (Tan1), terminal ear 1 (Tel), and vanishing tassel 2 (Vt2). As used herein, a "mutation" includes an edit—i.e., a mutation introduced via a genome editing technique.

As used herein, a "brachytic plant" refers to a plant having a mutated, edited or suppressed brachytic gene and a short semi-dwarf height and stature relative to a control plant (e.g., a wild-type sibling plant comprising all other traits except the brachytic trait) due to a shortening of the average internode length. Such a brachytic mutant plant can have a short semi-dwarf height and stature due to a shortening of the average internode length. As used herein, a "brachytic gene", "BR gene" or "br gene", or "Br gene" refers to any brachytic gene in a corn plant that when suppressed, mutated or edited to reduce its expression or function can result in a shorter, semi-dwarf corn plant and phenotype.

In an aspect, at least 10% of the corn plants in a field are brachytic corn plants. In an aspect, at least 20% of the corn plants in a field are brachytic corn plants. In an aspect, at least 30% of the corn plants in a field are brachytic corn plants. In an aspect, at least 40% of the corn plants in a field are brachytic corn plants. In an aspect, at least 50% of the corn plants in a field are brachytic corn plants. In an aspect, at least 60% of the corn plants in a field are brachytic corn plants. In an aspect, at least 70% of the corn plants in a field are brachytic corn plants. In an aspect, at least 80% of the corn plants in a field are brachytic corn plants. In an aspect, at least 90% of the corn plants in a field are brachytic corn plants. In an aspect, 100% of the corn plants in a field are brachytic corn plants.

In an aspect, between 1% and 100% of the corn plants in a field are brachytic corn plants. In an aspect, between 10% and 100% of the corn plants in a field are brachytic corn plants. In an aspect, between 20% and 100% of the corn plants in a field are brachytic corn plants. In an aspect, between 30% and 100% of the corn plants in a field are brachytic corn plants. In an aspect, between 40% and 100% of the corn plants in a field are brachytic corn plants. In an aspect, between 50% and 100% of the corn plants in a field are brachytic corn plants. In an aspect, between 60% and 100% of the corn plants in a field are brachytic corn plants. In an aspect, between 70% and 100% of the corn plants in a field are brachytic corn plants. In an aspect, between 80% and 100% of the corn plants in a field are brachytic corn plants. In an aspect, between 90% and 100% of the corn plants in a field are brachytic corn plants.

It will be appreciated in the art that dwarf, semi-dwarf, and brachytic plants can be inbred or hybrid plants.

Three brachytic mutants have been isolated in maize to date: brachytic1 (br1), brachytic2 (br2) and brachytic3 (br3). brachytic3 is also known as *brevis* plant 1 (Bv1). Both br1 and br3 mutations cause a reduction in corn plant height which has been thought too severe for commercial exploitation due to potential impacts on yield. In contrast, the br2 mutant has particular agronomic potential because of shortening of the internodes of the lower stalk without an obvious reduction in other plant organs. In addition, br2 lines exhibit an unusual stalk strength and tolerance to wind lodging, while the leaves are often darker and persist longer in the active green than those of the wild-type plants. The br2 phenotype is insensitive to treatment with Gibberellins, auxins, brassinosteroids and cytokinins, suggesting that the biosynthesis of these hormones is not modified by the br2 mutation. Multani et al. identified the genomic sequence of the br2 gene and deposited it under GenBank Accession No. AY366085. See Multani et al., Science, 302:81-84 (2003). Br2 was annotated to encode a putative protein similar to adenosine triphosphate (ATP)-binding cassette transporters of the multidrug resistant (MDR) class of P-glycoproteins (PGPs). Pilu et al. reported a br2-23 allele having an 8-bp deletion in the 3' end of the br2 gene and claimed a direct relationship between this deletion and the brachytic phenotype in their br2-23 plants. See Pilu et al., Molecular Breeding, 20:83-91(2007). Other brachytic gene alleles are known in the art which may be used according to embodiments of the present disclosure.

In some aspects, a brachytic, dwarf, or semi-dwarf corn plant comprises a reduced level of Br2 mRNA and/or protein compared to a control corn plant not having the brachytic allele. In other aspects, the corn plants or seeds comprise reduced Br2 protein activity compared to a control plant not having the brachytic allele. In some aspects, the height of a brachytic, dwarf, or semi-dwarf plant comprising a brachytic allele at maturity is reduced by at least 5%, at least 10%, at least 20%, at least 30%, at least 40%, at least 50%, at least 60%, or at least 70% compared to a control plant not having a brachytic allele. In another aspect, the yield of a brachytic, dwarf, or semi-dwarf corn plant comprising a brachytic allele is equal to or more than the yield of a control plant not having the brachytic allele.

In an aspect, at least 10% of the corn plants in a field comprise a mutation in a br2 locus as compared to a wildtype br2 locus. In an aspect, at least 20% of the corn plants in a field comprise a mutation in a br2 locus as compared to a wildtype br2 locus. In an aspect, at least 30% of the corn plants in a field comprise a mutation in a br2 locus as compared to a wildtype br2 locus. In an aspect, at least 40% of the corn plants in a field comprise a mutation in a br2 locus as compared to a wildtype br2 locus. In an aspect, at least 50% of the corn plants in a field comprise a mutation in a br2 locus as compared to a wildtype br2 locus. In an aspect, at least 60% of the corn plants in a field comprise a mutation in a br2 locus as compared to a wildtype br2 locus. In an aspect, at least 70% of the corn plants in a field comprise a mutation in a br2 locus as compared to a wildtype br2 locus. In an aspect, at least 80% of the corn plants in a field comprise a mutation in a br2 locus as compared to a wildtype br2 locus. In an aspect, at least 90% of the corn plants in a field comprise a mutation in a br2 locus as compared to a wildtype br2 locus. In an aspect, 100% of the corn plants in a field comprise a mutation in a br2 locus as compared to a wildtype br2 locus.

In an aspect, between 1% and 100% of the corn plants in a field comprise a mutation in a br2 locus as compared to a wildtype br2 locus. In an aspect, between 10% and 100% of the corn plants in a field comprise a mutation in a br2 locus as compared to a wildtype br2 locus. In an aspect, between 20% and 100% of the corn plants in a field comprise a mutation in a br2 locus as compared to a wildtype br2 locus. In an aspect, between 30% and 100% of the corn plants in a field comprise a mutation in a br2 locus as compared to a wildtype br2 locus. In an aspect, between 40% and 100% of the corn plants in a field comprise a mutation in a br2 locus as compared to a wildtype br2 locus. In an aspect, between 50% and 100% of the corn plants in a field comprise a mutation in a br2 locus as compared to a wildtype br2 locus. In an aspect, between 60% and 100% of the corn plants in a field comprise a mutation in a br2 locus as compared to a wildtype br2 locus. In an aspect, between 70% and 100% of the corn plants in a field comprise a mutation in a br2 locus as compared to a wildtype br2 locus. In an aspect, between 80% and 100% of the corn plants in a field comprise a mutation in a br2 locus as compared to a wildtype br2 locus. In an aspect, between 90% and 100% of the corn plants in a field comprise a mutation in a br2 locus as compared to a wildtype br2 locus.

In another aspect, a corn plant provided herein comprises a non-transgene or non-transposon mediated mutation in a BR gene reducing the activity of the BR gene. In a further aspect, a corn plant provided herein comprises a recessive, non-transgenic BR mutant allele. In another aspect, a corn plant provided herein comprises a heterologous polynucleotide capable of suppressing expression of a BR gene or an mRNA transcribed therefrom. In another aspect, a corn plant provided herein comprises a heterologous polynucleotide capable of suppressing expression of a BR1 gene or an mRNA transcribed therefrom. In another aspect, a corn plant provided herein comprises a heterologous polynucleotide capable of suppressing expression of a BR2 gene or an mRNA transcribed therefrom. In another aspect, a corn plant provided herein comprises a heterologous polynucleotide capable of suppressing expression of a BR3 gene or an mRNA transcribed therefrom. Additional details about corn plants and altering the expression of BR genes can be found in PCT Application No. PCT/US2016/029492 and PCT/US2017/067888, which are incorporated herein by reference in their entirety.

In an aspect, at least 10% of the corn plants in a field comprise a heterologous polynucleotide capable of suppressing expression of a br2 gene or an mRNA transcribed therefrom. In an aspect, at least 20% of the corn plants in a field comprise a heterologous polynucleotide capable of suppressing expression of a br2 gene or an mRNA transcribed therefrom. In an aspect, at least 30% of the corn plants in a field comprise a heterologous polynucleotide capable of suppressing expression of a br2 gene or an mRNA transcribed therefrom. In an aspect, at least 40% of the corn plants in a field comprise a heterologous polynucleotide capable of suppressing expression of a br2 gene or an mRNA transcribed therefrom. In an aspect, at least 50% of the corn plants in a field comprise a heterologous polynucleotide capable of suppressing expression of a br2 gene or an mRNA transcribed therefrom. In an aspect, at least 60% of the corn plants in a field comprise a heterologous polynucleotide capable of suppressing expression of a br2 gene or an mRNA transcribed therefrom. In an aspect, at least 70% of the corn plants in a field comprise a heterologous polynucleotide capable of suppressing expression of a br2 gene or an mRNA transcribed therefrom. In an aspect, at least 80% of the corn plants in a field comprise a heterologous polynucleotide capable of suppressing expression of a br2 gene or an mRNA transcribed therefrom. In an aspect, at least 90% of the corn plants in a field comprise a heterologous polynucleotide capable of suppressing expression of a br2 gene or an mRNA transcribed therefrom. In an aspect, 100% of the corn plants in a field comprise a heterologous polynucleotide capable of suppressing expression of a br2 gene or an mRNA transcribed therefrom.

In an aspect, between 1% and 100% of the corn plants in a field comprise a heterologous polynucleotide capable of suppressing expression of a br2 gene or an mRNA transcribed therefrom. In an aspect, between 10% and 100% of the corn plants in a field comprise a heterologous polynucleotide capable of suppressing expression of a br2 gene or an mRNA transcribed therefrom. In an aspect, between 20% and 100% of the corn plants in a field comprise a heterologous polynucleotide capable of suppressing expression of a br2 gene or an mRNA transcribed therefrom. In an aspect, between 30% and 100% of the corn plants in a field comprise a heterologous polynucleotide capable of suppressing expression of a br2 gene or an mRNA transcribed therefrom. In an aspect, between 40% and 100% of the corn plants in a field comprise a heterologous polynucleotide capable of suppressing expression of a br2 gene or an mRNA transcribed therefrom. In an aspect, between 50% and 100% of the corn plants in a field comprise a heterologous polynucleotide capable of suppressing expression of a br2 gene or an mRNA transcribed therefrom. In an aspect, between 60% and 100% of the corn plants in a field comprise a heterologous polynucleotide capable of suppressing expression of a br2 gene or an mRNA transcribed therefrom. In an aspect, between 70% and 100% of the corn plants in a field comprise a heterologous polynucleotide capable of suppressing expression of a br2 gene or an mRNA transcribed therefrom. In an aspect, between 80% and 100% of the corn plants in a field comprise a heterologous polynucleotide capable of suppressing expression of a br2 gene or an mRNA transcribed therefrom. In an aspect, between 90% and 100% of the corn plants in a field comprise a heterologous polynucleotide capable of suppressing expression of a br2 gene or an mRNA transcribed therefrom.

Certain biosynthetic enzymes (e.g., GA20 oxidase and GA3 oxidase) and catabolic enzymes (e.g., GA2 oxidase) in the GA pathway participate in GA synthesis and degradation, respectively, to affect active GA levels in plant tissues. Thus, in addition to suppression of certain GA20 oxidase genes, it is further proposed that suppression of a GA3 oxidase gene in a constitutive or tissue-specific or tissue-preferred manner can also produce corn plants having a short stature phenotype and increased lodging resistance, with possible increased yield, but without off-types in the ear.

Without being bound by theory, it is proposed that suppression of GA20 or GA3 oxidase gene(s) and/or targeting of a subset of one or more GA oxidase gene(s) can be effective in achieving a short stature, semi-dwarf phenotype with increased resistance to lodging, but without reproductive off-types in the ear. It is further proposed, without being limited by theory, that suppression of GA20 and/or GA3 oxidase gene(s) through constitutive expression or in active GA-producing tissues, such as the vascular and/or leaf tissues of the plant, can produce a short-stature plant with increased lodging resistance, but without significant off-types in reproductive tissues. Expression of a GA20 or GA3 oxidase suppression element using a constitutive, vascular and/or leaf promoter can be sufficient and effective at producing plants with the short stature phenotype, while avoiding potential off-types in reproductive tissues that were previously observed with GA mutants in corn. For example, GA20 and/or GA3 oxidase gene(s) can be targeted for suppression using a vascular promoter, such as a rice tungro bacilliform virus (RTBV) promoter, that drives expression in vascular tissues of plants. The expression pattern of the RTBV promoter is enriched in vascular tissues of corn plants relative to non-vascular tissues, which is sufficient to produce a semi-dwarf phenotype in corn plants when operably linked to a suppression element targeting GA20 and GA3 oxidase gene(s). Lowering of active GA levels in tissue(s) of a corn plant, such as in the stalk, stem, or internode(s) of corn plant, that produce active GAs can reduce plant height and increase lodging resistance, and avoid off-types in the reproductive tissues of the plant, such as in the female (ear) or male (tassel) tissues of the plant.

Without being limited by theory, it is proposed that short stature, semi-dwarf phenotypes in corn plants can result from a sufficient level of expression of a suppression construct targeting certain GA oxidase gene(s) in active GA-producing tissue(s) of the plant. For targeted suppression of certain GA20 oxidase genes in corn, restricting the pattern of expression to avoid reproductive ear tissues may not be necessary to avoid reproductive off-types in the developing ear. However, expression of a GA20 oxidase suppression construct at low levels, and/or in a limited number of plant tissues, can be insufficient to cause a significant short stature, semi-dwarf phenotype. Given that the observed semi-dwarf phenotype with targeted GA20 oxidase suppression is the result of shortening the stem internodes of the plant, suppression of GA20 oxidase genes in at least some stem tissues was not sufficient to cause shortening of the internodes and reduced plant height. Without being bound by theory, it is proposed that suppression of certain GA oxidase gene(s) in tissue(s) and/or cell(s) of the plant where active GAs are produced, and not necessarily in stem or internode tissue(s), can be sufficient to produce semi-dwarf plants, even though the short stature trait is due to shortening of the stem internodes. Given that GAs can migrate through the vasculature of the plant, manipulating GA oxidase genes in plant tissue(s) where active GAs are produced can result in a short stature, semi-dwarf plant, even though this may be largely achieved by suppressing the level of active GAs produced in non-stem tissues (i.e., away from the site of action in the stem where reduced internode elongation leads to the semi-dwarf phenotype). Indeed, suppression of certain GA20 oxidase genes in leaf tissues causes a moderate semi-dwarf phenotype in corn plants. Given that expression of a GA20 oxidase suppression construct with several different "stem" promoters did not produce the semi-dwarf phenotype in corn, it is noteworthy that expression of the same GA20 oxidase suppression construct with a vascular promoter was effective at consistently producing the semi-dwarf phenotype with a high degree of penetrance across events and germplasms. A semi-dwarf phenotype was also observed with expression of the same GA20 oxidase suppression construct using other vascular promoters and with various constitutive promoters without any observable off-types. Additional details about corn plants and altering the expression of GA20 oxidase and GA3 oxidase genes can be found in PCT Application No. PCT/US2017/047405 and PCT/US2019/018133, which are incorporated herein by reference in their entirety.

In an aspect, at least 10% of the corn plants in a field comprise a mutation in a GA20 oxidase locus as compared to a wildtype GA20 oxidase locus. In an aspect, at least 20% of the corn plants in a field comprise a mutation in a GA20 oxidase locus as compared to a wildtype GA20 oxidase locus. In an aspect, at least 30% of the corn plants in a field comprise a mutation in a GA20 oxidase locus as compared to a wildtype GA20 oxidase locus. In an aspect, at least 40% of the corn plants in a field comprise a mutation in a GA20 oxidase locus as compared to a wildtype GA20 oxidase locus. In an aspect, at least 50% of the corn plants in a field comprise a mutation in a GA20 oxidase locus as compared to a wildtype GA20 oxidase locus. In an aspect, at least 60% of the corn plants in a field comprise a mutation in a GA20 oxidase locus as compared to a wildtype GA20 oxidase locus. In an aspect, at least 70% of the corn plants in a field comprise a mutation in a GA20 oxidase locus as compared to a wildtype GA20 oxidase locus. In an aspect, at least 80% of the corn plants in a field comprise a mutation in a GA20 oxidase locus as compared to a wildtype GA20 oxidase locus. In an aspect, at least 90% of the corn plants in a field comprise a mutation in a GA20 oxidase locus as compared to a wildtype GA20 oxidase locus. In an aspect, 100% of the corn plants in a field comprise a mutation in a GA20 oxidase locus as compared to a wildtype GA20 oxidase locus.

In an aspect, between 1% and 100% of the corn plants in a field comprise a mutation in a GA20 oxidase locus as compared to a wildtype GA20 oxidase locus. In an aspect, between 10% and 100% of the corn plants in a field comprise a mutation in a GA20 oxidase locus as compared to a wildtype GA20 oxidase locus. In an aspect, between 20% and 100% of the corn plants in a field comprise a mutation in a GA20 oxidase locus as compared to a wildtype GA20 oxidase locus. In an aspect, between 30% and 100% of the corn plants in a field comprise a mutation in a GA20 oxidase locus as compared to a wildtype GA20 oxidase locus. In an aspect, between 40% and 100% of the corn plants in a field comprise a mutation in a GA20 oxidase locus as compared to a wildtype GA20 oxidase locus. In an aspect, between 50% and 100% of the corn plants in a field comprise a mutation in a GA20 oxidase locus as compared to a wildtype GA20 oxidase locus. In an aspect, between 60% and 100% of the corn plants in a field comprise a mutation in a GA20 oxidase locus as compared to a wildtype GA20 oxidase locus. In an aspect, between 70% and 100% of the corn plants in a field comprise a mutation in a GA20 oxidase locus as compared to a wildtype GA20 oxidase locus. In an aspect, between 80% and 100% of the corn plants in a field comprise a mutation in a GA20 oxidase locus as compared to a wildtype GA20 oxidase locus. In an aspect, between 90% and 100% of the corn plants in a field comprise a mutation in a GA20 oxidase locus as compared to a wildtype GA20 oxidase locus.

In an aspect, at least 10% of the corn plants in a field comprise a mutation in a GA3 oxidase locus as compared to a wildtype GA3 oxidase locus. In an aspect, at least 20% of the corn plants in a field comprise a mutation in a GA3 oxidase locus as compared to a wildtype GA3 oxidase locus. In an aspect, at least 30% of the corn plants in a field comprise a mutation in a GA3 oxidase locus as compared to a wildtype GA3 oxidase locus. In an aspect, at least 40% of the corn plants in a field comprise a mutation in a GA3 oxidase locus as compared to a wildtype GA3 oxidase locus. In an aspect, at least 50% of the corn plants in a field comprise a mutation in a GA3 oxidase locus as compared to a wildtype GA3 oxidase locus. In an aspect, at least 60% of the corn plants in a field comprise a mutation in a GA3 oxidase locus as compared to a wildtype GA3 oxidase locus. In an aspect, at least 70% of the corn plants in a field comprise a mutation in a GA3 oxidase locus as compared to a wildtype GA3 oxidase locus. In an aspect, at least 80% of the corn plants in a field comprise a mutation in a GA3 oxidase locus as compared to a wildtype GA3 oxidase locus. In an aspect, at least 90% of the corn plants in a field comprise a mutation in a GA3 oxidase locus as compared to a wildtype GA3 oxidase locus. In an aspect, 100% of the corn plants in a field comprise a mutation in a GA3 oxidase locus as compared to a wildtype GA3 oxidase locus.

In an aspect, between 1% and 100% of the corn plants in a field comprise a mutation in a GA3 oxidase locus as compared to a wildtype GA3 oxidase locus. In an aspect, between 10% and 100% of the corn plants in a field comprise a mutation in a GA3 oxidase locus as compared to a wildtype GA3 oxidase locus. In an aspect, between 20% and 100% of the corn plants in a field comprise a mutation in a GA3 oxidase locus as compared to a wildtype GA3 oxidase locus. In an aspect, between 30% and 100% of the corn plants in a field comprise a mutation in a GA3 oxidase locus as compared to a wildtype GA3 oxidase locus. In an aspect, between 40% and 100% of the corn plants in a field comprise a mutation in a GA3 oxidase locus as compared to a wildtype GA3 oxidase locus. In an aspect, between 50% and 100% of the corn plants in a field comprise a mutation in a GA3 oxidase locus as compared to a wildtype GA3 oxidase locus. In an aspect, between 60% and 100% of the corn plants in a field comprise a mutation in a GA3 oxidase locus as compared to a wildtype GA3 oxidase locus. In an aspect, between 70% and 100% of the corn plants in a field comprise a mutation in a GA3 oxidase locus as compared to a wildtype GA3 oxidase locus. In an aspect, between 80% and 100% of the corn plants in a field comprise a mutation in a GA3 oxidase locus as compared to a wildtype GA3 oxidase locus. In an aspect, between 90% and 100% of the corn plants in a field comprise a mutation in a GA3 oxidase locus as compared to a wildtype GA3 oxidase locus.

In an aspect, at least 10% of the corn plants in a field comprise a heterologous polynucleotide capable of suppressing expression of a GA20 oxidase gene or an mRNA transcribed therefrom. In an aspect, at least 20% of the corn plants in a field comprise a heterologous polynucleotide capable of suppressing expression of a GA20 oxidase gene or an mRNA transcribed therefrom. In an aspect, at least 30% of the corn plants in a field comprise a heterologous polynucleotide capable of suppressing expression of a GA20 oxidase gene or an mRNA transcribed therefrom. In an aspect, at least 40% of the corn plants in a field comprise a heterologous polynucleotide capable of suppressing expression of a GA20 oxidase gene or an mRNA transcribed therefrom. In an aspect, at least 50% of the corn plants in a field comprise a heterologous polynucleotide capable of suppressing expression of a GA20 oxidase gene or an mRNA transcribed therefrom. In an aspect, at least 60% of the corn plants in a field comprise a heterologous polynucleotide capable of suppressing expression of a GA20 oxidase gene or an mRNA transcribed therefrom. In an aspect, at least 70% of the corn plants in a field comprise a heterologous polynucleotide capable of suppressing expression of a GA20 oxidase gene or an mRNA transcribed therefrom. In an aspect, at least 80% of the corn plants in a field comprise a heterologous polynucleotide capable of suppressing expression of a GA20 oxidase gene or an mRNA transcribed therefrom. In an aspect, at least 90% of the corn plants in a field comprise a heterologous polynucleotide capable of suppressing expression of a GA20 oxidase gene or an mRNA transcribed therefrom. In an aspect, 100% of the corn plants in a field comprise a heterologous polynucleotide capable of suppressing expression of a GA20 oxidase gene or an mRNA transcribed therefrom.

In an aspect, between 1% and 100% of the corn plants in a field comprise a heterologous polynucleotide capable of suppressing expression of a GA20 oxidase gene or an mRNA transcribed therefrom. In an aspect, between 10% and 100% of the corn plants in a field comprise a heterologous polynucleotide capable of suppressing expression of a GA20 oxidase gene or an mRNA transcribed therefrom. In an aspect, between 20% and 100% of the corn plants in a field comprise a heterologous polynucleotide capable of suppressing expression of a GA20 oxidase gene or an mRNA transcribed therefrom. In an aspect, between 30% and 100% of the corn plants in a field comprise a heterologous polynucleotide capable of suppressing expression of a GA20 oxidase gene or an mRNA transcribed therefrom. In an aspect, between 40% and 100% of the corn plants in a field comprise a heterologous polynucleotide capable of suppressing expression of a GA20 oxidase gene or an mRNA transcribed therefrom. In an aspect, between 50% and 100% of the corn plants in a field comprise a heterologous polynucleotide capable of suppressing expression of a GA20 oxidase gene or an mRNA transcribed therefrom. In an aspect, between 60% and 100% of the corn plants in a field comprise a heterologous polynucleotide capable of suppressing expression of a GA20 oxidase gene or an mRNA transcribed therefrom. In an aspect, between 70% and 100% of the corn plants in a field comprise a heterologous polynucleotide capable of suppressing expression of a GA20 oxidase gene or an mRNA transcribed therefrom. In an aspect, between 80% and 100% of the corn plants in a field comprise a heterologous polynucleotide capable of suppressing expression of a GA20 oxidase gene or an mRNA transcribed therefrom. In an aspect, between 90% and 100% of the corn plants in a field comprise a heterologous polynucleotide capable of suppressing expression of a GA20 oxidase gene or an mRNA transcribed therefrom.

In an aspect, at least 10% of the corn plants in a field comprise a heterologous polynucleotide capable of suppressing expression of a GA3 oxidase gene or an mRNA transcribed therefrom. In an aspect, at least 20% of the corn plants in a field comprise a heterologous polynucleotide capable of suppressing expression of a GA3 oxidase gene or an mRNA transcribed therefrom. In an aspect, at least 30% of the corn plants in a field comprise a heterologous polynucleotide capable of suppressing expression of a GA3 oxidase gene or an mRNA transcribed therefrom. In an aspect, at least 40% of the corn plants in a field comprise a heterologous polynucleotide capable of suppressing expression of a GA3 oxidase gene or an mRNA transcribed therefrom. In an aspect, at least 50% of the corn plants in a field comprise a heterologous polynucleotide capable of suppressing expression of a GA3 oxidase gene or an mRNA transcribed therefrom. In an aspect, at least 60% of the corn plants in a field comprise a heterologous polynucleotide capable of suppressing expression of a GA3 oxidase gene or an mRNA transcribed therefrom. In an aspect, at least 70% of the corn plants in a field comprise a heterologous polynucleotide capable of suppressing expression of a GA3 oxidase gene or an mRNA transcribed therefrom. In an aspect, at least 80% of the corn plants in a field comprise a heterologous polynucleotide capable of suppressing expression of a GA3 oxidase gene or an mRNA transcribed therefrom. In an aspect, at least 90% of the corn plants in a field comprise a heterologous polynucleotide capable of suppressing expression of a GA3 oxidase gene or an mRNA transcribed therefrom. In an aspect, 100% of the corn plants in a field comprise a heterologous polynucleotide capable of suppressing expression of a GA3 oxidase gene or an mRNA transcribed therefrom.

In an aspect, between 1% and 100% of the corn plants in a field comprise a heterologous polynucleotide capable of suppressing expression of a GA3 oxidase gene or an mRNA transcribed therefrom. In an aspect, between 10% and 100% of the corn plants in a field comprise a heterologous polynucleotide capable of suppressing expression of a GA3 oxidase gene or an mRNA transcribed therefrom. In an aspect, between 20% and 100% of the corn plants in a field comprise a heterologous polynucleotide capable of suppressing expression of a GA3 oxidase gene or an mRNA transcribed therefrom. In an aspect, between 30% and 100% of the corn plants in a field comprise a heterologous polynucleotide capable of suppressing expression of a GA3 oxidase gene or an mRNA transcribed therefrom. In an aspect, between 40% and 100% of the corn plants in a field comprise a heterologous polynucleotide capable of suppressing expression of a GA3 oxidase gene or an mRNA transcribed therefrom. In an aspect, between 50% and 100% of the corn plants in a field comprise a heterologous polynucleotide capable of suppressing expression of a GA3 oxidase gene or an mRNA transcribed therefrom. In an aspect, between 60% and 100% of the corn plants in a field comprise a heterologous polynucleotide capable of suppressing expression of a GA3 oxidase gene or an mRNA transcribed therefrom. In an aspect, between 70% and 100% of the corn plants in a field comprise a heterologous polynucleotide capable of suppressing expression of a GA3 oxidase gene or an mRNA transcribed therefrom. In an aspect, between 80% and 100% of the corn plants in a field comprise a heterologous polynucleotide capable of suppressing expression of a GA3 oxidase gene or an mRNA transcribed therefrom. In an aspect, between 90% and 100% of the corn plants in a field comprise a heterologous polynucleotide capable of suppressing expression of a GA3 oxidase gene or an mRNA transcribed therefrom.

A corn field is considered to be "harvested" when at least one ear has been removed from most, all, or a majority of the corn plants in the field. A corn plant(s) is/are considered to be "harvested" when at least one ear has been removed from the corn plant(s), or at least from most or a majority of the corn plants.

As used herein, a "field" refers to an outdoor location that is suitable for growing corn, and a "corn field" refers to a field that has been planted with a plurality or population of corn plants. The field or location can be irrigated or non-irrigated. A corn field can comprise a land area planted with corn seed and/or at least one corn plant or a plurality of corn plants, which can be at one or more stages of development. According to some aspects, a plurality of corn plants in a field can be at a homogeneous or the same (or nearly homogeneous or nearly the same) stage of development, such that the plurality of corn plants have approximately the same height. In an aspect, a corn plant provided herein is planted in a field.

In another aspect, a corn plant provided herein is not planted in the field, but is planted indoors, such as in a greenhouse, and/or in a container holding a growth medium or soil.

A corn field can comprise one or more rows of corn plants of the same or different lengths. As used herein, a "row" comprises a plurality of corn plants in a linear or near linear arrangement. In an aspect, a row comprises at least two corn plants. Without being limiting, a row of corn plants is planted in a line, and if a corn field comprises two or more rows, they are typically planted parallel to each other. A corn field can comprise one or more rows of corn plants where the rows are of the same or different lengths. Without being limiting, a corn field comprises at least 1 row of corn plants. In another aspect, a corn field comprises at least 10 rows of corn plants. In another aspect, a corn field comprises at least 50 rows of corn plants. In another aspect, a corn field comprises at least 500 rows of corn plants. In another aspect, a corn field comprises at least 1,000 rows of corn plants. In another aspect, a corn field comprises at least 5,000 rows of corn plants. In another aspect, a corn field comprises at least 10,000 rows of corn plants.

In an aspect, a corn field comprises rows that are spaced at least 5 inches apart. In another aspect, a corn field comprises rows that are spaced at least 10 inches apart. In a further aspect, a corn field comprises rows that are spaced at least 15 inches apart. In an aspect, a corn field comprises rows of corn plants that are spaced at least 20 inches apart. In another aspect, a corn field comprises rows of corn that are spaced at least 25 inches apart. In another aspect, a corn field comprises rows of corn that are spaced at least 30 inches apart. According to some aspects, a corn field can comprise two or more pluralities of corn plants with the pluralities of corn plants being planted with different corn varieties, at different times, at different densities, in different arrangements (e.g., in rows or scattered or random placement), and/or at different row spacings and/or row lengths, such that the pluralities of corn plants have different heights, spacings, etc., at different time points during the growing season, although each plurality of corn plants can be relatively uniform with respect to plant height and other growth metrics.

In an aspect, a field comprises a single plot. In another aspect, a field comprises multiple plots. In another aspect, one or more edges of a field are bordered by a fence. In another aspect, one or more edges of a field are unfenced. In another aspect, one or more edges of a field are bordered by hedges. In an aspect, a field comprises a physically contiguous space. In another aspect, the field comprises a physically non-contiguous space. In still another aspect, the field comprises a biologically contiguous space. As used herein, a "biologically contiguous space" refers to a space where the pollen can move from one section of a field to another. In an aspect, a biologically contiguous field is physically contiguous. In another aspect, a biologically contiguous field is physically non-contiguous (e.g., plots within the field or a single plot within the field can be separated by a structure, without being limiting, such as a road, creek, irrigation ditch, trail, hedgerow, fence, irrigation pipes, fallow field, empty field, or non-corn plants).

In an aspect, a field comprises at least 0.5 acres. In an aspect, a field comprises at least 1 acre. In another aspect, a field comprises at least 5 acres. In another aspect, a field comprises at least 10 acres. In another aspect, a field comprises at least 15 acres. In another aspect, a field comprises at least 20 acres. In another aspect, a field comprises at least 25 acres. In another aspect, a field comprises at least 30 acres. In another aspect, a field comprises at least 35 acres. In another aspect, a field comprises at least 40 acres. In another aspect, a field comprises at least 45 acres. In another aspect, a field comprises at least 50 acres. In another aspect, a field comprises at least 75 acres. In another aspect, a field comprises at least 100 acres. In another aspect, a field comprises at least 150 acres. In another aspect, a field comprises at least 200 acres. In another aspect, a field comprises at least 250 acres. In another aspect, a field comprises at least 300 acres. In another aspect, a field comprises at least 350 acres. In another aspect, a field comprises at least 400 acres. In another aspect, a field comprises at least 450 acres. In another aspect, a field comprises at least 500 acres. In another aspect, a field comprises at least 750 acres. In another aspect, a field comprises at least 1000 acres. In another aspect, a field comprises at least 1500 acres. In another aspect, a field comprises at least 2000 acres. In another aspect, a field comprises at least 2500 acres. In another aspect, a field comprises at least 3000 acres. In another aspect, a field comprises at least 4000 acres. In another aspect, a field comprises at least 5000 acres. In another aspect, a field comprises at least 10,000 acres.

In an aspect, a field comprises between 0.5 acres and 10,000 acres. In another aspect, a field comprises between 1 acre and 10,000 acres. In another aspect, a field comprises between 5 acres and 10,000 acres. In another aspect, a field comprises between 10 acres and 10,000 acres. In another aspect, a field comprises between 15 acres and 10,000 acres. In another aspect, a field comprises between 20 acres and 10,000 acres. In another aspect, a field comprises between 25 acres and 10,000 acres. In another aspect, a field comprises between 30 acres and 10,000 acres. In another aspect, a field comprises between 35 acres and 10,000 acres. In another aspect, a field comprises between 40 acres and 10,000 acres. In another aspect, a field comprises between 45 acres and 10,000 acres. In another aspect, a field comprises between 50 acres and 10,000 acres. In another aspect, a field comprises between 75 acres and 10,000 acres. In another aspect, a field comprises between 100 acres and 10,000 acres. In another aspect, a field comprises between 150 acres and 10,000 acres. In another aspect, a field comprises between 200 acres and 10,000 acres. In another aspect, a field comprises between 250 acres and 10,000 acres. In another aspect, a field comprises between 300 acres and 10,000 acres. In another aspect, a field comprises between 350 acres and 10,000 acres. In another aspect, a field comprises between 400 acres and 10,000 acres. In another aspect, a field comprises between 450 acres and 10,000 acres. In another aspect, a field comprises between 500 acres and 10,000 acres. In another aspect, a field comprises between 750 acres and 10,000 acres. In another aspect, a field comprises between 1000 acres and 10,000 acres. In another aspect, a field comprises between 1500 acres and 10,000 acres. In another aspect, a field comprises between 2000 acres and 10,000 acres. In another aspect, a field comprises between 2500 acres and 10,000 acres. In another aspect, a field comprises between 3000 acres and 10,000 acres. In another aspect, a field comprises between 4000 acres and 10,000 acres. In another aspect, a field comprises between 5000 acres and 10,000 acres. In another aspect, a field comprises between 1 acre and 5000 acres. In another aspect, a field comprises between 1 acre and 2500 acres. In another aspect, a field comprises between 1 acre and 1000 acres. In another aspect, a field comprises between 1 acre and 500 acres. In another aspect, a field comprises between 1 acre and 250 acres. In another aspect, a field comprises between 1 acre and 100 acres. In another aspect, a field comprises between 1 acre and 75 acres. In another aspect, a field comprises between 1 acre and 50 acres. In another aspect, a field comprises between 1 acre and 25 acres. In another aspect, a field comprises between 1 acre and 10 acres.

In an aspect, a corn field can further comprise plants other than corn plants including, without being limiting, cotton, alfalfa, sunflowers, sorghum, wheat, barley, oat, rice, rye, soybean, vegetables (e.g., potato, tomato, carrot), grass (e.g., bluegrass, Triticale), and weeds.

In an aspect, a corn field comprises a density of at least 10,000 corn plants per acre. In another aspect, a corn field comprises a density of at least 15,000 corn plants per acre. In another aspect, a corn field comprises a density of at least 20,000 corn plants per acre. In another aspect, a corn field comprises a density of at least 22,000 corn plants per acre. In another aspect, a corn field comprises a density of at least 24,000 corn plants per acre. In another aspect, a corn field comprises a density of at least 26,000 corn plants per acre. In another aspect, a corn field comprises a density of at least 28,000 corn plants per acre. In another aspect, a corn field comprises a density of at least 30,000 corn plants per acre. In another aspect, a corn field comprises a density of at least 32,000 corn plants per acre. In another aspect, a corn field comprises a density of at least 34,000 corn plants per acre. In another aspect, a corn field comprises a density of at least 36,000 corn plants per acre. In another aspect, a corn field comprises a density of at least 38,000 corn plants per acre. In another aspect, a corn field comprises a density of at least 40,000 corn plants per acre. In another aspect, a corn field comprises a density of at least 42,000 corn plants per acre. In another aspect, a corn field comprises a density of at least 44,000 corn plants per acre. In another aspect, a corn field comprises a density of at least 46,000 corn plants per acre. In another aspect, a corn field comprises a density of at least 48,000 corn plants per acre. In another aspect, a corn field comprises a density of at least 50,000 corn plants per acre. In another aspect, a corn field comprises a density of at least 52,000 corn plants per acre. In another aspect, a corn field comprises a density of at least 54,000 corn plants per acre. In another aspect, a corn field comprises a density of at least 56,000 corn plants per acre. In another aspect, a corn field comprises a density of at least 58,000 corn plants per acre. In another aspect, a corn field comprises a density of at least 60,000 corn plants per acre.

In an aspect, a corn field comprises a density of between 10,000 and 50,000 corn plants per acre. In an aspect, a corn field comprises a density of between 10,000 and 40,000 corn plants per acre. In an aspect, a corn field comprises a density of between 10,000 and 30,000 corn plants per acre. In an aspect, a corn field comprises a density of between 10,000 and 25,000 corn plants per acre. In an aspect, a corn field comprises a density of between 10,000 and 20,000 corn plants per acre. In an aspect, a corn field comprises a density of between 20,000 corn plants and 60,000 corn plants per acre. In an aspect, a corn field comprises a density of between 20,000 corn plants and 58,000 corn plants per acre. In an aspect, a corn field comprises a density of between 20,000 corn plants and 55,000 corn plants per acre. In an aspect, a corn field comprises a density of between 20,000 corn plants and 50,000 corn plants per acre. In an aspect, a corn field comprises a density of between 20,000 corn plants and 45,000 corn plants per acre. In an aspect, a corn field comprises a density of between 20,000 corn plants and 42,000 corn plants per acre. In an aspect, a corn field comprises a density of between 20,000 corn plants and 40,000 corn plants per acre. In an aspect, a corn field comprises a density of between 20,000 corn plants and 38,000 corn plants per acre. In an aspect, a corn field comprises a density of between 20,000 corn plants and 36,000 corn plants per acre. In an aspect, a corn field comprises a density of between 20,000 corn plants and 34,000 corn plants per acre. In an aspect, a corn field comprises a density of between 20,000 corn plants and 32,000 corn plants per acre. In an aspect, a corn field comprises a density of between 20,000 corn plants and 30,000 corn plants per acre. In an aspect, a corn field comprises a density of between 24,000 corn plants and 58,000 corn plants per acre. In an aspect, a corn field comprises a density of between 38,000 corn plants and 60,000 corn plants per acre. In an aspect, a corn field comprises a density of between 38,000 corn plants and 50,000 corn plants per acre.

In an aspect, a corn field comprises at least 10 corn plants. In another aspect, a corn field comprises at least 10 corn plants per acre. In an aspect, a corn field comprises at least 100 corn plants. In another aspect, a corn field comprises at least 100 corn plants per acre. In an aspect, a corn field comprises at least 500 corn plants. In another aspect, a corn field comprises at least 500 corn plants per acre. In an aspect, a corn field comprises at least 1000 corn plants. In another aspect, a corn field comprises at least 1000 corn plants per acre. In an aspect, a corn field comprises at least 5000 corn plants. In another aspect, a corn field comprises at least 5000 corn plants per acre. In an aspect, a corn field comprises at least 10,000 corn plants. In an aspect, a corn field comprises at least 10,000 corn plants per acre. In an aspect, a corn field comprises at least 12,000 corn plants. In an aspect, a corn field comprises at least 12,000 corn plants per acre. In an aspect, a corn field comprises at least 15,000 corn plants. In an aspect, a corn field comprises at least 15,000 corn plants per acre. In an aspect, a corn field comprises at least 18,000 corn plants. In an aspect, a corn field comprises at least 18,000 corn plants per acre. In an aspect, a corn field comprises at least 20,000 corn plants. In an aspect, a corn field comprises at least 20,000 corn plants per acre. In an aspect, a corn field comprises at least 22,000 corn plants. In an aspect, a corn field comprises at least 22,000 corn plants per acre. In an aspect, a corn field comprises at least 24,000 corn plants. In an aspect, a corn field comprises at least 24,000 corn plants per acre. In an aspect, a corn field comprises at least 26,000 corn plants. In an aspect, a corn field comprises at least 26,000 corn plants per acre. In an aspect, a corn field comprises at least 28,000 corn plants. In an aspect, a corn field comprises at least 28,000 corn plants per acre. In an aspect, a corn field comprises at least 30,000 corn plants. In an aspect, a corn field comprises at least 30,000 corn plants per acre. In an aspect, a corn field comprises at least 32,000 corn plants. In an aspect, a corn field comprises at least 32,000 corn plants per acre. In an aspect, a corn field comprises at least 34,000 corn plants. In an aspect, a corn field comprises at least 34,000 corn plants per acre. In an aspect, a corn field comprises at least 36,000 corn plants. In an aspect, a corn field comprises at least 36,000 corn plants per acre. In an aspect, a corn field comprises at least 38,000 corn plants. In an aspect, a corn field comprises at least 38,000 corn plants per acre. In an aspect, a corn field comprises at least 40,000 corn plants. In an aspect, a corn field comprises at least 40,000 corn plants per acre. In an aspect, a corn field comprises at least 42,000 corn plants. In an aspect, a corn field comprises at least 42,000 corn plants per acre. In an aspect, a corn field comprises at least 44,000 corn plants. In an aspect, a corn field comprises at least 44,000 corn plants per acre. In an aspect, a corn field comprises at least 46,000 corn plants. In an aspect, a corn field comprises at least 46,000 corn plants per acre. In an aspect, a corn field comprises at least 48,000 corn plants. In an aspect, a corn field comprises at least 48,000 corn plants per acre. In an aspect, a corn field comprises at least 50,000 corn plants. In an aspect, a corn field comprises at least 50,000 corn plants per acre. In an aspect, a corn field comprises at least 52,000 corn plants. In an aspect, a corn field comprises at least 52,000 corn plants per acre. In an aspect, a corn field comprises at least 54,000 corn plants. In an aspect, a corn field comprises at least 54,000 corn plants per acre. In an aspect, a corn field comprises at least 56,000 corn plants. In an aspect, a corn field comprises at least 56,000 corn plants per acre. In an aspect, a corn field comprises at least 58,000 corn plants. In an aspect, a corn field comprises at least 58,000 corn plants per acre. In an aspect, a corn field comprises at least 60,000 corn plants. In an aspect, a corn field comprises at least 60,000 corn plants per acre.

In an aspect, a corn field comprises between 10,000 corn plants per acre and 50,000 corn plants per acre. In an aspect, a corn field comprises between 10,000 corn plants per acre and 40,000 corn plants per acre. In an aspect, a corn field comprises between 10,000 corn plants per acre and 30,000 corn plants per acre. In an aspect, a corn field comprises between 10,000 corn plants per acre and 25,000 corn plants per acre. In an aspect, a corn field comprises between 10,000 corn plants per acre and 20,000 corn plants per acre. In an aspect, a corn field comprises between 20,000 corn plants per acre and 60,000 corn plants per acre. In an aspect, a corn field comprises between 20,000 corn plants per acre and 58,000 corn plants per acre. In an aspect, a corn field comprises between 20,000 corn plants per acre and 55,000 corn plants per acre. In an aspect, a corn field comprises between 20,000 corn plants per acre and 50,000 corn plants per acre. In an aspect, a corn field comprises between 20,000 corn plants per acre and 45,000 corn plants per acre. In an aspect, a corn field comprises between 20,000 corn plants per acre and 42,000 corn plants per acre. In an aspect, a corn field comprises between 20,000 corn plants per acre and 40,000 corn plants per acre. In an aspect, a corn field comprises between 20,000 corn plants per acre and 38,000 corn plants per acre. In an aspect, a corn field comprises between 20,000 corn plants per acre and 36,000 corn plants per acre. In an aspect, a corn field comprises between 20,000 corn plants per acre and 34,000 corn plants per acre. In an aspect, a corn field comprises between 20,000 corn plants per acre and 32,000 corn plants per acre. In an aspect, a corn field comprises between 20,000 corn plants per acre and 30,000 corn plants per acre. In an aspect, a corn field comprises between 24,000 corn plants per acre and 58,000 corn plants per acre. In an aspect, a corn field comprises between 38,000 corn plants per acre and 60,000 corn plants per acre. In an aspect, a corn field comprises between 38,000 corn plants per acre and 50,000 corn plants per acre.

In an aspect, a corn field comprises at least 0.5 acres. In another aspect, a corn field comprises at least 1 acre. In another aspect, a corn field comprises at least 3 acres. In another aspect, a corn field comprises at least 5 acres. In another aspect, a corn field comprises at least 10 acres. In another aspect, a corn field comprises at least 15 acres. In another aspect, a corn field comprises at least 20 acres. In another aspect, a corn field comprises at least 25 acres. In another aspect, a corn field comprises at least 50 acres. In another aspect, a corn field comprises at least 75 acres. In another aspect, a corn field comprises at least 100 acres. In another aspect, a corn field comprises at least 150 acres. In another aspect, a corn field comprises at least 200 acres. In another aspect, a corn field comprises at least 250 acres. In another aspect, a corn field comprises at least 300 acres. In another aspect, a corn field comprises at least 350 acres. In another aspect, a corn field comprises at least 400 acres. In another aspect, a corn field comprises at least 500 acres. In another aspect, a corn field comprises at least 750 acres. In another aspect, a corn field comprises at least 1000 acres. In another aspect, a corn field comprises at least 2500 acres. In another aspect, a corn field comprises at least 5 acres. In another aspect, a corn field comprises at least 5000 acres.

In an aspect, a corn field comprises between 0.5 acres and 5000 acres. In another aspect, a corn field comprises between 1 acre and 5000 acres. In another aspect, a corn field comprises between 5 acres and 5000 acres. In another aspect, a corn field comprises between 10 acres and 5000 acres. In another aspect, a corn field comprises between 25 acres and 5000 acres. In another aspect, a corn field comprises between 50 acres and 5000 acres. In another aspect, a corn field comprises between 100 acres and 5000 acres. In another aspect, a corn field comprises between 200 acres and 5000 acres. In another aspect, a corn field comprises between 500 acres and 5000 acres. In another aspect, a corn field comprises between 1000 acres and 5000 acres. In another aspect, a corn field comprises between 1 acre and 500 acres. In another aspect, a corn field comprises between 1 acre and 400 acres. In another aspect, a corn field comprises between 1 acre and 300 acres. In another aspect, a corn field comprises between 1 acre and 250 acres. In another aspect, a corn field comprises between 1 acre and 200 acres. In another aspect, a corn field comprises between 1 acre and 150 acres. In another aspect, a corn field comprises between 1 acre and 100 acres. In another aspect, a corn field comprises between 1 acre and 75 acres. In another aspect, a corn field comprises between 1 acre and 50 acres. In another aspect, a corn field comprises between 1 acre and 25 acres. In another aspect, a corn field comprises between 10 acres and 25 acres. In another aspect, a corn field comprises between 10 acres and 50 acres. In another aspect, a corn field comprises between 10 acres and 100 acres. In another aspect, a corn field comprises between 10 acres and 250 acres. In another aspect, a corn field comprises between 10 acres and 500 acres. In another aspect, a corn field comprises between 100 acres and 250 acres. In another aspect, a corn field comprises between 100 acres and 500 acres.

As used herein, the term "yield" refers to the amount of harvested plant material or grain, such as kernels or seeds, but may also or instead include the amount of biomass harvested (including for example, stalk, leaves, and/or kernels), from the plant(s). Harvested grain can be used in a variety of applications including food processing, animal feed, etc., and biomass may be used for a variety of applications including sileage, biofuel, etc., as known in the art. In an aspect, yield is measured as the amount of biomass or sileage harvested from the plant(s). In another aspect, yield is measured in bushels per acre. In another aspect, yield is measured in average number of kernels per ear. In still another aspect, yield is measured in grams per dry kernel. In still another aspect, yield is measured in terms of average kernel weight and the average number of kernels per ear. In still another aspect, yield is measured in Standard Seed Units (SSU) per acre. One SSU for corn is equivalent to 80,000 corn seed kernels. The number of Standard Seed Units (SSUs) is appropriate for seed production since it quantifies the number of plants that can potentially be grown from the quantity of seeds, whereas yield takes into account both seed number and seed size.

In an aspect, the average yield of a corn field comprises at least 100 bushels per acre. In an aspect, the average yield of a corn field comprises at least 120 bushels per acre. In an aspect, the average yield of a corn field comprises at least 130 bushels per acre. In an aspect, the average yield of a corn field comprises at least 140 bushels per acre. In an aspect, the average yield of a corn field comprises at least 150 bushels per acre. In an aspect, the average yield of a corn field comprises at least 160 bushels per acre. In an aspect, the average yield of a corn field comprises at least 170 bushels per acre. In an aspect, the average yield of a corn field comprises at least 180 bushels per acre. In an aspect, the average yield of a corn field comprises at least 190 bushels per acre. In an aspect, the average yield of a corn field comprises at least 200 bushels per acre. In an aspect, the average yield of a corn field comprises at least 210 bushels per acre. In an aspect, the average yield of a corn field comprises at least 220 bushels per acre. In an aspect, the average yield of a corn field comprises at least 230 bushels per acre. In an aspect, the average yield of a corn field comprises at least 240 bushels per acre. In an aspect, the average yield of a corn field comprises at least 250 bushels per acre. In an aspect, the average yield of a corn field comprises at least 260 bushels per acre.

In an aspect, the average yield of a corn field comprises between 100 bushels per acre and 260 bushels per acre. In an aspect, the average yield of a corn field comprises between 120 bushels per acre and 260 bushels per acre. In an aspect, the average yield of a corn field comprises between 140 bushels per acre and 260 bushels per acre. In an aspect, the average yield of a corn field comprises between 160 bushels per acre and 260 bushels per acre. In an aspect, the average yield of a corn field comprises between 180 bushels per acre and 260 bushels per acre. In an aspect, the average yield of a corn field comprises between 200 bushels per acre and 260 bushels per acre. In an aspect, the average yield of a corn field comprises between 220 bushels per acre and 260 bushels per acre. In an aspect, the average yield of a corn field comprises between 240 bushels per acre and 260 bushels per acre. In an aspect, the average yield of a corn field comprises between 100 bushels per acre and 200 bushels per acre. In an aspect, the average yield of a corn field comprises between 150 bushels per acre and 250 bushels per acre. In an aspect, the average yield of a corn field comprises between 150 bushels per acre and 200 bushels per acre.

In an aspect, the average yield of a corn field harvested at least 30 days, at least 40 days, at least 50 days, at least 60 days, at least 70 days, at least 80 days at, least 90 days, at least 100 days, or at least 110 days after fertilization or silking is within 5% of the average yield of a corn field comprising plants of the same genetic background harvested between 20 and 30 days after fertilization or silking. In an aspect, the average yield of a corn field harvested at least 30 days, at least 40 days, at least 50 days, at least 60 days, at least 70 days, at least 80 days at, least 90 days, at least 100 days, or at least 110 days after fertilization or silking is within 10% of the average yield of a corn field comprising plants of the same genetic background harvested between 20 and 30 days after fertilization or silking. In an aspect, the average yield of a corn field harvested at least 30 days, at least 40 days, at least 50 days, at least 60 days, at least 70 days, at least 80 days, at least 90 days, at least 100 days, or at least 110 days after fertilization or silking is within 15% of the average yield of a corn field comprising plants of the same genetic background harvested between 20 and 30 days after fertilization or silking. In an aspect, the average yield of a corn field harvested at least 30 days, at least 40 days, at least 50 days, at least 60 days, at least 70 days, at least 80 days, at least 90 days, at least 100 days, or at least 110 days after fertilization or silking is within 20% of the average yield of a corn field comprising plants of the same genetic background harvested between 20 and 30 days after fertilization or silking. In an aspect, the average yield of a corn field comprising plants of the same genetic background harvested at least 30 days, at least 40 days, at least 50 days, at least 60 days, at least 70 days, at least 80 days, at least 90 days, at least 100 days, or at least 110 days after fertilization or silking is within 25% of the average yield of a corn field comprising plants of the same genetic background harvested between 20 and 30 days after fertilization or silking. In an aspect, the average yield of a corn field comprising plants of the same genetic background harvested at least 30 days, at least 40 days, at least 50 days, at least 60 days, at least 70 days, at least 80 days, at least 90 days, at least 100 days, or at least 110 days after fertilization or silking is within 30% of the average yield of a corn field comprising plants of the same genetic background harvested between 20 and 30 days after fertilization or silking.

Kernel moisture content can be measured by any means typically used in the art. Non-limiting examples for measuring kernel moisture content include the use of an electronic grain moisture tester (e.g., infrared monitors); direct measurement of water content via a chemical reaction (e.g., the Karl Fischer method); and drying whole kernel samples and measuring weight loss during drying.

In an aspect, a method provided herein comprises harvesting corn plants comprising an average kernel moisture content of less than or equal to 30%. In an aspect, a method provided herein comprises harvesting corn plants comprising an average kernel moisture content of less than or equal to 29%. In an aspect, a method provided herein comprises harvesting corn plants comprising an average kernel moisture content of less than or equal to 28%. In an aspect, a method provided herein comprises harvesting corn plants comprising an average kernel moisture content of less than or equal to 27%. In an aspect, a method provided herein comprises harvesting corn plants comprising an average kernel moisture content of less than or equal to 26%. In an aspect, a method provided herein comprises harvesting corn plants comprising an average kernel moisture content of less than or equal to 25%. In an aspect, a method provided herein comprises harvesting corn plants comprising an average kernel moisture content of less than or equal to 24%. In an aspect, a method provided herein comprises harvesting corn plants comprising an average kernel moisture content of less than or equal to 23%. In an aspect, a method provided herein comprises harvesting corn plants comprising an average kernel moisture content of less than or equal to 22%. In an aspect, a method provided herein comprises harvesting corn plants comprising an average kernel moisture content of less than or equal to 21%. In an aspect, a method provided herein comprises harvesting corn plants comprising an average kernel moisture content of less than or equal to 20%. In an aspect, a method provided herein comprises harvesting corn plants comprising an average kernel moisture content of less than or equal to 19%. In an aspect, a method provided herein comprises harvesting corn plants comprising an average kernel moisture content of less than or equal to 18%. In an aspect, a method provided herein comprises harvesting corn plants comprising an average kernel moisture content of less than or equal to 17%. In an aspect, a method provided herein comprises harvesting corn plants comprising an average kernel moisture content of less than or equal to 16%. In an aspect, a method provided herein comprises harvesting corn plants comprising an average kernel moisture content of less than or equal to 15%. In an aspect, a method provided herein comprises harvesting corn plants comprising an average kernel moisture content of less than or equal to 14%. In an aspect, a method provided herein comprises harvesting corn plants comprising an average kernel moisture content of less than or equal to 13%. In an aspect, a method provided herein comprises harvesting corn plants comprising an average kernel moisture content of less than or equal to 12%. In an aspect, a method provided herein comprises harvesting corn plants comprising an average kernel moisture content of less than or equal to 10%. Each of the above average kernel moisture content ranges may also apply to the kernel moisture content of a corn plant, such as the kernel moisture content of a corn plant of a plurality of corn plants.

In an aspect, a method provided herein comprises harvesting corn plants comprising an average kernel moisture content of between 10% and 30%. In an aspect, a method provided herein comprises harvesting corn plants comprising an average kernel moisture content of between 11% and 30%. In an aspect, a method provided herein comprises harvesting corn plants comprising an average kernel moisture content of between 12% and 30%. In an aspect, a method provided herein comprises harvesting corn plants comprising an average kernel moisture content of between 13% and 30%. In an aspect, a method provided herein comprises harvesting corn plants comprising an average kernel moisture content of between 14% and 30%. In an aspect, a method provided herein comprises harvesting corn plants comprising an average kernel moisture content of between 15% and 30%. In an aspect, a method provided herein comprises harvesting corn plants comprising an average kernel moisture content of between 16% and 30%. In an aspect, a method provided herein comprises harvesting corn plants comprising an average kernel moisture content of between 17% and 30%.

In an aspect, a method provided herein comprises harvesting corn plants comprising an average kernel moisture content of between 18% and 30%. In an aspect, a method provided herein comprises harvesting corn plants comprising an average kernel moisture content of between 19% and 30%. In an aspect, a method provided herein comprises harvesting corn plants comprising an average kernel moisture content of between 20% and 30%. In an aspect, a method provided herein comprises harvesting corn plants comprising an average kernel moisture content of between 21% and 30%. In an aspect, a method provided herein comprises harvesting corn plants comprising an average kernel moisture content of between 22% and 30%. In an aspect, a method provided herein comprises harvesting corn plants comprising an average kernel moisture content of between 23% and 30%. In an aspect, a method provided herein comprises harvesting corn plants comprising an average kernel moisture content of between 24% and 30%. In an aspect, a method provided herein comprises harvesting corn plants comprising an average kernel moisture content of between 25% and 30%. In an aspect, a method provided herein comprises harvesting corn plants comprising an average kernel moisture content of between 26% and 30%. In an aspect, a method provided herein comprises harvesting corn plants comprising an average kernel moisture content of between 27% and 30%. In an aspect, a method provided herein comprises harvesting corn plants comprising an average kernel moisture content of between 28% and 30%. In an aspect, a method provided herein comprises harvesting corn plants comprising an average kernel moisture content of between 29% and 30%. Each of the above average kernel moisture content ranges may also apply to the kernel moisture content of a corn plant of the plurality of corn plants.

In an aspect, a method provided herein comprises harvesting corn plants comprising an average kernel moisture content of between 10% and 25%. In an aspect, a method provided herein comprises harvesting corn plants comprising an average kernel moisture content of between 10% and 20%. In an aspect, a method provided herein comprises harvesting corn plants comprising an average kernel moisture content of between 10% and 15%. In an aspect, a method provided herein comprises harvesting corn plants comprising an average kernel moisture content of between 10% and 13%. In an aspect, a method provided herein comprises harvesting corn plants comprising an average kernel moisture content of between 13% and 25%. In an aspect, a method provided herein comprises harvesting corn plants comprising an average kernel moisture content of between 13% and 20%. In an aspect, a method provided herein comprises harvesting corn plants comprising an average kernel moisture content of between 13% and 15%. In an aspect, a method provided herein comprises harvesting corn plants comprising an average kernel moisture content of between 15% and 25%. In an aspect, a method provided herein comprises harvesting corn plants comprising an average kernel moisture content of between 15% and 20%. In an aspect, a method provided herein comprises harvesting corn plants comprising an average kernel moisture content of between 20% and 25%. Each of the above average kernel moisture content ranges may also apply to the kernel moisture content of a corn plant of the plurality of corn plants.

In an aspect, methods are provided comprising harvesting a plurality of corn plants in a field at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 20 days, at least 25 days, at least 30 days, at least 35 days, at least 40 days, at least 45 days, at least 50 days, at least 55 days, at least 60 days, at least 65 days, at least 70 days, at least 75 days, at least 80 days, at least 90 days, at least 95 days, at least 100 days, or at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, or at least 15 weeks after a desired or acceptable kernel moisture content or average kernel moisture content is reached (without being limiting, for example, between 10% and 30%, between 10% and 25%, between 13% and 25%, between 15% and 25%, between 10% and 20%, or between 15% and 30% or any other specific moisture content percentage within any of such moisture content ranges or as provided herein), which may comprise measuring the moisture content of one or more ears or kernels of a corn plant of the plurality of corn plants in the field (or an average kernel moisture content for two or more corn plants of the plurality of corn plants), and harvesting the plurality of corn plants if the desired or acceptable kernel moisture content or desired or acceptable average kernel moisture content is reached.

As used herein, an "acceptable" or "desired" kernel moisture content can be any specific kernel moisture content percentage, or any kernel moisture content within a range of kernel moisture content percentages, provided herein. An "average kernel moisture content" for a plurality of corn plants is the average moisture content of kernels from two or more corn plants, such as from two or more corn plants of a plurality of corn plants. An "average kernel moisture content" for a single corn plant is the average moisture content of two or more kernels from a corn plant.

Leaf moisture content or stalk moisture content can also be measured using techniques standard in the art.

In an aspect, a method provided herein comprises harvesting corn plants comprising an average stalk moisture content and/or an average leaf moisture content of equal to or less than 30%. In an aspect, a method provided herein comprises harvesting corn plants comprising an average stalk moisture content and/or an average leaf moisture content of equal to or less than 25%. In an aspect, a method provided herein comprises harvesting corn plants comprising an average stalk moisture content and/or an average leaf moisture content of equal to or less than 20%. In an aspect, a method provided herein comprises harvesting corn plants comprising an average stalk moisture content and/or an average leaf moisture content of equal to or less than 15%. In an aspect, a method provided herein comprises harvesting corn plants comprising an average stalk moisture content and/or an average leaf moisture content of equal to or less than 10%. Each of the above average stalk and/or leaf moisture content ranges may also apply to the stalk or leaf moisture content of a corn plant of the plurality of corn plants.

In another aspect, a method provided herein comprises harvesting corn plants comprising an average stalk moisture content and/or an average leaf moisture content of between 10% and 30%. In another aspect, a method provided herein comprises harvesting corn plants comprising an average stalk moisture content and/or an average leaf moisture content of between 15% and 30%. In another aspect, a method provided herein comprises harvesting corn plants comprising an average stalk moisture content and/or an average leaf moisture content of between 15% and 25% or a stalk or leaf moisture content of a corn plant, such as a corn plant of a plurality of corn plants, of between 15% and 25%.

In an aspect, a method provided herein comprises harvesting a plurality of corn plants from a field where fewer than or equal to 95% of the corn plants have lodged at the time of harvest. In an aspect, a method provided herein comprises harvesting a plurality of corn plants from a field where fewer than or equal to 90% of the corn plants have lodged at the time of harvest. In an aspect, a method provided herein comprises harvesting a plurality of corn plants from a field where fewer than or equal to 80% of the corn plants have lodged at the time of harvest. In an aspect, a method provided herein comprises harvesting a plurality of corn plants from a field where fewer than or equal to 70% of the corn plants have lodged at the time of harvest. In an aspect, a method provided herein comprises harvesting a plurality of corn plants from a field where fewer than or equal to 60% of the corn plants have lodged at the time of harvest. In an aspect, a method provided herein comprises harvesting a plurality of corn plants from a field where fewer than or equal to 50% of the corn plants have lodged at the time of harvest. In an aspect, a method provided herein comprises harvesting a plurality of corn plants from a field where fewer than or equal to 45% of the corn plants have lodged at the time of harvest. In an aspect, a method provided herein comprises harvesting a plurality of corn plants from a field where fewer than or equal to 40% of the corn plants have lodged at the time of harvest. In an aspect, a method provided herein comprises harvesting a plurality of corn plants from a field where fewer than or equal to 35% of the corn plants have lodged at the time of harvest. In an aspect, a method provided herein comprises harvesting a plurality of corn plants from a field where fewer than or equal to 30% of the corn plants have lodged at the time of harvest. In an aspect, a method provided herein comprises harvesting a plurality of corn plants from a field where fewer than or equal to 25% of the corn plants have lodged at the time of harvest. In an aspect, a method provided herein comprises harvesting a plurality of corn plants from a field where fewer than or equal to 20% of the corn plants have lodged at the time of harvest. In an aspect, a method provided herein comprises harvesting a plurality of corn plants from a field where fewer than or equal to 15% of the corn plants have lodged at the time of harvest. In an aspect, a method provided herein comprises harvesting a plurality of corn plants from a field where fewer than or equal to 10% of the corn plants have lodged at the time of harvest. In an aspect, a method provided herein comprises harvesting a plurality of corn plants from a field where fewer than or equal to 5% of the corn plants have lodged at the time of harvest. In an aspect, a method provided herein comprises harvesting a plurality of corn plants from a field where fewer than or equal to 1% of the corn plants have lodged at the time of harvest. In an aspect, a method provided herein comprises harvesting a plurality of corn plants from a field where 0% of the corn plants have lodged at the time of harvest.

In an aspect, a method provided herein comprises harvesting a plurality of corn plants from a field where between 0% and 100% of the corn plants have lodged at the time of harvest. In an aspect, a method provided herein comprises harvesting a plurality of corn plants from a field where between 0% and 90% of the corn plants have lodged at the time of harvest. In an aspect, a method provided herein comprises harvesting a plurality of corn plants from a field where between 0% and 80% of the corn plants have lodged at the time of harvest. In an aspect, a method provided herein comprises harvesting a plurality of corn plants from a field where between 0% and 70% of the corn plants have lodged at the time of harvest. In an aspect, a method provided herein comprises harvesting a plurality of corn plants from a field where between 0% and 60% of the corn plants have lodged at the time of harvest. In an aspect, a method provided herein comprises harvesting a plurality of corn plants from a field where between 0% and 50% of the corn plants have lodged at the time of harvest. In an aspect, a method provided herein comprises harvesting a plurality of corn plants from a field where between 0% and 40% of the corn plants have lodged at the time of harvest. In an aspect, a method provided herein comprises harvesting a plurality of corn plants from a field where between 0% and 30% of the corn plants have lodged at the time of harvest. In an aspect, a method provided herein comprises harvesting a plurality of corn plants from a field where between 0% and 25% of the corn plants have lodged at the time of harvest. In an aspect, a method provided herein comprises harvesting a plurality of corn plants from a field where between 0% and 20% of the corn plants have lodged at the time of harvest. In an aspect, a method provided herein comprises harvesting a plurality of corn plants from a field where between 0% and 15% of the corn plants have lodged at the time of harvest. In an aspect, a method provided herein comprises harvesting a plurality of corn plants from a field where between 0% and 10% of the corn plants have lodged at the time of harvest. In an aspect, a method provided herein comprises harvesting a plurality of corn plants from a field where between 10% and 50% of the corn plants have lodged at the time of harvest. In an aspect, a method provided herein comprises harvesting a plurality of corn plants from a field where between 10% and 20% of the corn plants have lodged at the time of harvest. In an aspect, a method provided herein comprises harvesting a plurality of corn plants from a field where between 10% and 30% of the corn plants have lodged at the time of harvest. In an aspect, a method provided herein comprises harvesting a plurality of corn plants from a field where between 20% and 50% of the corn plants have lodged at the time of harvest. In an aspect, a method provided herein comprises harvesting a plurality of corn plants from a field where between 30% and 50% of the corn plants have lodged at the time of harvest. In an aspect, a method provided herein comprises harvesting a plurality of corn plants from a field where between 40% and 50% of the corn plants have lodged at the time of harvest.

The height of a corn plant can be determined based on a variety of anatomical locations on a corn plant. In an aspect, the height of a corn plant is measured as the distance between the top of the soil or ground and the ligule or collar of the uppermost fully-expanded leaf of a corn plant. As used herein, a "fully-expanded leaf" is a leaf where the leaf blade is exposed, and both the ligule and auricle are visible at the blade/sheath boundary. In another aspect, the height of a corn plant is measured as the distance between the top of the soil or ground and the upper leaf surface of the leaf farthest from the soil or ground. In a further aspect, the height of a corn plant is measured as the distance between the top of the soil or ground and the arch of the highest corn leaf that is at least 50% developed. In still a further aspect, the height of a corn plant is measured as the distance between the top of the soil or ground and the anatomical part of the corn plant that is farthest from the top of the soil or ground. Exemplary, non-limiting methods of measuring plant height include comparing photographs of corn plants to a height reference, or physically measuring individual corn plants with a suitable ruler. If not otherwise stated, the height of a corn plant for the present disclosure is measured as the distance between the top of the soil or ground and the collar of the uppermost fully-expanded leaf of a corn plant. If not otherwise stated, all descriptions herein with regard to the plant height of a population of plants can refer to either the average plant height among the population of plants or, if stated, the percentage(s) of plants among the population of plants.

Short stature corn plants typically have improved standability and reduced lodging as compared to taller corn plants. In an aspect, the average height of corn plants in a corn field provided herein is less than or equal to 1.9 meters at the time of harvest. In an aspect, the average height of corn plants in a corn field provided herein is less than or equal to 1.8 meters at the time of harvest. In an aspect, the average height of corn plants in a corn field provided herein is less than or equal to 1.7 meters at the time of harvest. In an aspect, the average height of corn plants in a corn field provided herein is less than or equal to 1.6 meters at the time of harvest. In an aspect, the average height of corn plants in a corn field provided herein is less than or equal to 1.5 meters at the time of harvest. In an aspect, the average height of corn plants in a corn field provided herein is less than or equal to 1.4 meters at the time of harvest. In an aspect, the average height of corn plants in a corn field provided herein is less than or equal to 1.3 meters at the time of harvest.

In an aspect, the average height of corn plants in a corn field provided herein is less than or equal to 1.9 meters at R1 stage, R2 stage, R3 stage, R4 stage, or R5 stage or later. In an aspect, the average height of corn plants in a corn field provided herein is less than or equal to 1.8 meters at R1 stage, R2 stage, R3 stage, R4 stage, or R5 stage or later. In an aspect, the average height of corn plants in a corn field provided herein is less than or equal to 1.7 meters at R1 stage, R2 stage, R3 stage, R4 stage, or R5 stage or later. In an aspect, the average height of corn plants in a corn field provided herein is less than or equal to 1.6 meters at R1 stage, R2 stage, R3 stage, R4 stage, or R5 stage or later. In an aspect, the average height of corn plants in a corn field provided herein is less than or equal to 1.5 meters at R1 stage, R2 stage, R3 stage, R4 stage, or R5 stage or later. In an aspect, the average height of corn plants in a corn field provided herein is less than or equal to 1.4 meters at R1 stage, R2 stage, R3 stage, R4 stage, or R5 stage or later. In an aspect, the average height of corn plants in a corn field provided herein is less than or equal to 1.3 meters at R1 stage, R2 stage, R3 stage, R4 stage, or R5 stage or later. In an aspect, the average height of corn plants in a corn field provided herein is less than or equal to 1.2 meters at R1 stage, R2 stage, R3 stage, R4 stage, or R5 stage or later. In an aspect, the average height of corn plants in a corn field provided herein is less than or equal to 1.1 meters at R1 stage, R2 stage, R3 stage, R4 stage, or R5 stage or later.

In an aspect, the average height of corn plants in a corn field provided herein is between 1.1 meters and 1.9 meters at the time of harvest. In an aspect, the average height of corn plants in a corn field provided herein is between 1.3 meters and 1.8 meters at the time of harvest. In an aspect, the average height of corn plants in a corn field provided herein is between 1.3 meters and 1.7 meters at the time of harvest. In an aspect, the average height of corn plants in a corn field provided herein is between 1.4 meters and 1.7 meters at the time of harvest. In an aspect, the average height of corn plants in a corn field provided herein is between 1.5 meters and 1.7 meters at the time of harvest. In an aspect, the average height of corn plants in a corn field provided herein is between 1.6 meters and 1.7 meters at the time of harvest.

Corn leaves consist of four main anatomical parts: a proximal sheath, a ligule, an auricle, and a distal blade. The sheath wraps around the stem and younger leaves, while the blade is flattened in the mediolateral axis (midrib to margin). The ligule and auricle are found at the blade/sheath boundary; the ligule is an adaxial (upper) membranous structure that acts as a collar around the stem, and the auricle is a projection on the lower surface of the blade base that connects the blade to the sheath. Stages of corn plant growth are divided into vegetative (V) stages and reproductive (R) stages. Upon germination, a corn plant is said to be in VE stage (emergence). Once the first leaf collar (e.g., the ligule) is visible, the corn plant is in the V1 stage. The emergence of the second leaf collar signifies V2 stage; the emergence of the third leaf collar signifies the V3 stage; and so on until the tassel emerges. For example, if twelve leaf collars are visible, the plant is a V12 stage plant. Once the bottom-most branch of the tassel emerges the plant is in VT stage, which is the final vegetative stage. The reproductive stage of growth occurs after the vegetative stage. The number of vegetative stages prior to VT stage can vary by environment and corn line. The first reproductive stage (R1; silking stage; "silking") occurs when silk is visible outside the husk leaves surrounding an ear of corn. R2 (blistering stage) occurs when corn kernels are white on the outside and are filled with a clear liquid inside. R3 (milk stage) occurs when the kernels are yellow on the outside and are filled with a milky white fluid inside. R4 (dough stage) occurs when the kernels are filled with a thick, or pasty, fluid. In some corn lines the cob will also turn pink or red at this stage. R5 (dent stage) occurs when a majority of the kernels are at least partially dented. The final reproductive stage, R6 (physiological maturity), occurs when the kernels have attained their maximum dry weight.

In an aspect, a method provided herein comprises harvesting a plurality of corn plants from a corn field at least 20 days after at least 50% of corn plants in the corn field have reached R3 stage. In an aspect, a method provided herein comprises harvesting a plurality of corn plants from a corn field at least 30 days after at least 50% of corn plants in the corn field have reached R3 stage. In an aspect, a method provided herein comprises harvesting a plurality of corn plants from a corn field at least 40 days after at least 50% of corn plants in the corn field have reached R3 stage. In an aspect, a method provided herein comprises harvesting a plurality of corn plants from a corn field at least 30 days, at least 40 days, at least 50 days, at least 60 days, at least 70 days, at least 80 days, at least 90 days, at least 100 days, or at least 110 days after at least 50%, at least 60%, at least 70%, at least 80%, at least 90% or 100% of corn plants in the corn field have reached R3 stage. In an aspect, a method provided herein comprises harvesting a plurality of corn plants from a corn field at least 55 days after at least 50% of corn plants in the corn field have reached R3 stage. In an aspect, a method provided herein comprises harvesting a plurality of corn plants from a corn field at least 60 days after at least 50% of corn plants in the corn field have reached R3 stage. In an aspect, a method provided herein comprises harvesting a plurality of corn plants from a corn field at least 75 days after at least 50% of corn plants in the corn field have reached R3 stage. In an aspect, a method provided herein comprises harvesting a plurality of corn plants from a corn field at least 90 days after at least 50% of corn plants in the corn field have reached R3 stage. In an aspect, a method provided herein comprises harvesting a plurality of corn plants from a corn field at least 120 days after at least 50% of corn plants in the corn field have reached R3 stage.

In an aspect, a method provided herein comprises harvesting a plurality of corn plants from a corn field between 20 days and 120 days after at least 50% of corn plants in the corn field have reached R3 stage. In an aspect, a method provided herein comprises harvesting a plurality of corn plants from a corn field between 30 days and 120 days after at least 50% of corn plants in the corn field have reached R3 stage. In an aspect, a method provided herein comprises harvesting a plurality of corn plants from a corn field between 40 days and 120 days after at least 50% of corn plants in the corn field have reached R3 stage. In an aspect, a method provided herein comprises harvesting a plurality of corn plants from a corn field between 50 days and 120 days after at least 50% of corn plants in the corn field have reached R3 stage. In an aspect, a method provided herein comprises harvesting a plurality of corn plants from a corn field between 50 days and 90 days after at least 50% of corn plants in the corn field have reached R3 stage. In an aspect, a method provided herein comprises harvesting a plurality of corn plants from a corn field between 50 days and 80 days after at least 50% of corn plants in the corn field have reached R3 stage. In an aspect, a method provided herein comprises harvesting a plurality of corn plants from a corn field between 50 days and 70 days after at least 50% of corn plants in the corn field have reached R3 stage. In an aspect, a method provided herein comprises harvesting a plurality of corn plants from a corn field between 60 days and 120 days after at least 50% of corn plants in the corn field have reached R3 stage. In an aspect, a method provided herein comprises harvesting a plurality of corn plants from a corn field between 60 days and 90 days after at least 50% of corn plants in the corn field have reached R3 stage.

In an aspect, a method provided herein comprises harvesting a plurality of corn plants from a corn field at least 20 days after at least 75% of corn plants in the corn field have reached R3 stage. In an aspect, a method provided herein comprises harvesting a plurality of corn plants from a corn field at least 30 days after at least 75% of corn plants in the corn field have reached R3 stage. In an aspect, a method provided herein comprises harvesting a plurality of corn plants from a corn field at least 40 days after at least 75% of corn plants in the corn field have reached R3 stage. In an aspect, a method provided herein comprises harvesting a plurality of corn plants from a corn field at least 30 days, at least 40 days, at least 50 days, at least 60 days, at least 70 days, at least 80 days, at least 90 days, at least 100 days, or at least 110 days after at least 75% of corn plants in the corn field have reached R3 stage. In an aspect, a method provided herein comprises harvesting a plurality of corn plants from a corn field at least 55 days after at least 75% of corn plants in the corn field have reached R3 stage. In an aspect, a method provided herein comprises harvesting a plurality of corn plants from a corn field at least 60 days after at least 75% of corn plants in the corn field have reached R3 stage. In an aspect, a method provided herein comprises harvesting a plurality of corn plants from a corn field at least 75 days after at least 75% of corn plants in the corn field have reached R3 stage. In an aspect, a method provided herein comprises harvesting a plurality of corn plants from a corn field at least 90 days after at least 75% of corn plants in the corn field have reached R3 stage. In an aspect, a method provided herein comprises harvesting a plurality of corn plants from a corn field at least 120 days after at least 75% of corn plants in the corn field have reached R3 stage.

In an aspect, a method provided herein comprises harvesting a plurality of corn plants from a corn field between 20 days and 120 days after at least 75% of corn plants in the corn field have reached R3 stage. In an aspect, a method provided herein comprises harvesting a plurality of corn plants from a corn field between 30 days and 120 days after at least 75% of corn plants in the corn field have reached R3 stage. In an aspect, a method provided herein comprises harvesting a plurality of corn plants from a corn field between 40 days and 120 days after at least 75% of corn plants in the corn field have reached R3 stage. In an aspect, a method provided herein comprises harvesting a plurality of corn plants from a corn field between 50 days and 120 days after at least 75% of corn plants in the corn field have reached R3 stage. In an aspect, a method provided herein comprises harvesting a plurality of corn plants from a corn field between 50 days and 90 days after at least 75% of corn plants in the corn field have reached R3 stage. In an aspect, a method provided herein comprises harvesting a plurality of corn plants from a corn field between 50 days and 80 days after at least 75% of corn plants in the corn field have reached R3 stage. In an aspect, a method provided herein comprises harvesting a plurality of corn plants from a corn field between 50 days and 70 days after at least 75% of corn plants in the corn field have reached R3 stage. In an aspect, a method provided herein comprises harvesting a plurality of corn plants from a corn field between 60 days and 120 days after at least 75% of corn plants in the corn field have reached R3 stage. In an aspect, a method provided herein comprises harvesting a plurality of corn plants from a corn field between 60 days and 90 days after at least 75% of corn plants in the corn field have reached R3 stage.

In an aspect, a method provided herein comprises harvesting a plurality of corn plants from a corn field at least 20 days after at least 90% of corn plants in the corn field have reached R3 stage. In an aspect, a method provided herein comprises harvesting a plurality of corn plants from a corn field at least 30 days after at least 90% of corn plants in the corn field have reached R3 stage. In an aspect, a method provided herein comprises harvesting a plurality of corn plants from a corn field at least 40 days after at least 90% of corn plants in the corn field have reached R3 stage. In an aspect, a method provided herein comprises harvesting a plurality of corn plants from a corn field at least 30 days, at least 40 days, at least 50 days, at least 60 days, at least 70 days, at least 80 days, at least 90 days, at least 100 days, or at least 110 days after at least 90% of corn plants in the corn field have reached R3 stage. In an aspect, a method provided herein comprises harvesting a plurality of corn plants from a corn field at least 55 days after at least 90% of corn plants in the corn field have reached R3 stage. In an aspect, a method provided herein comprises harvesting a plurality of corn plants from a corn field at least 60 days after at least 90% of corn plants in the corn field have reached R3 stage. In an aspect, a method provided herein comprises harvesting a plurality of corn plants from a corn field at least 75 days after at least 90% of corn plants in the corn field have reached R3 stage. In an aspect, a method provided herein comprises harvesting a plurality of corn plants from a corn field at least 90 days after at least 90% of corn plants in the corn field have reached R3 stage. In an aspect, a method provided herein comprises harvesting a plurality of corn plants from a corn field at least 120 days after at least 90% of corn plants in the corn field have reached R3 stage.

In an aspect, a method provided herein comprises harvesting a plurality of corn plants from a corn field between 20 days and 120 days after at least 90% of corn plants in the corn field have reached R3 stage. In an aspect, a method provided herein comprises harvesting a plurality of corn plants from a corn field between 30 days and 120 days after at least 90% of corn plants in the corn field have reached R3 stage. In an aspect, a method provided herein comprises harvesting a plurality of corn plants from a corn field between 40 days and 120 days after at least 90% of corn plants in the corn field have reached R3 stage. In an aspect, a method provided herein comprises harvesting a plurality of corn plants from a corn field between 50 days and 120 days after at least 90% of corn plants in the corn field have reached R3 stage. In an aspect, a method provided herein comprises harvesting a plurality of corn plants from a corn field between 50 days and 90 days after at least 90% of corn plants in the corn field have reached R3 stage. In an aspect, a method provided herein comprises harvesting a plurality of corn plants from a corn field between 50 days and 80 days after at least 90% of corn plants in the corn field have reached R3 stage. In an aspect, a method provided herein comprises harvesting a plurality of corn plants from a corn field between 50 days and 70 days after at least 90% of corn plants in the corn field have reached R3 stage. In an aspect, a method provided herein comprises harvesting a plurality of corn plants from a corn field between 60 days and 120 days after at least 90% of corn plants in the corn field have reached R3 stage. In an aspect, a method provided herein comprises harvesting a plurality of corn plants from a corn field between 60 days and 90 days after at least 90% of corn plants in the corn field have reached R3 stage.

As used herein, the term "fertilization" refers to the union of a male gamete and a female gamete to produce a kernel, or fertilized egg, following pollination. In an aspect, fertilization is performed by wind. In another aspect, fertilization is performed by human intervention. In another aspect, fertilization is performed by an animal or insect.

In an aspect, a method provided herein comprises harvesting a plurality of corn plants from a corn field at least 30 days after fertilization or silking of the plurality of corn plants. In an aspect, a method provided herein comprises harvesting a plurality of corn plants from a corn field at least 35 days after fertilization or silking of the plurality of corn plants. In an aspect, a method provided herein comprises harvesting a plurality of corn plants from a corn field at least 40 days after fertilization or silking of the plurality of corn plants. In an aspect, a method provided herein comprises harvesting a plurality of corn plants from a corn field at least 45 days after fertilization or silking of the plurality of corn plants. In an aspect, a method provided herein comprises harvesting a plurality of corn plants from a corn field at least 50 days after fertilization or silking of the plurality of corn plants. In an aspect, a method provided herein comprises harvesting a plurality of corn plants from a corn field at least 55 days after fertilization or silking of the plurality of corn plants. In an aspect, a method provided herein comprises harvesting a plurality of corn plants from a corn field at least 60 days after fertilization or silking of the plurality of corn plants. In an aspect, a method provided herein comprises harvesting a plurality of corn plants from a corn field at least 65 days after fertilization or silking of the plurality of corn plants. In an aspect, a method provided herein comprises harvesting a plurality of corn plants from a corn field at least 70 days after fertilization or silking of the plurality of corn plants. In an aspect, a method provided herein comprises harvesting a plurality of corn plants from a corn field at least 75 days after fertilization or silking of the plurality of corn plants. In an aspect, a method provided herein comprises harvesting a plurality of corn plants from a corn field at least 80 days after fertilization or silking of the plurality of corn plants. In an aspect, a method provided herein comprises harvesting a plurality of corn plants from a corn field at least 85 days after fertilization or silking of the plurality of corn plants. In an aspect, a method provided herein comprises harvesting a plurality of corn plants from a corn field at least 90 days after fertilization or silking of the plurality of corn plants. In an aspect, a method provided herein comprises harvesting a plurality of corn plants from a corn field at least 120 days after fertilization or silking of the plurality of corn plants.

In an aspect, a method provided herein comprises harvesting a plurality of corn plants from a corn field between 50 days and 120 days after fertilization or silking of the plurality of corn plants. In an aspect, a method provided herein comprises harvesting a plurality of corn plants from a corn field between 50 days and 90 days after fertilization or silking of the plurality of corn plants. In an aspect, a method provided herein comprises harvesting a plurality of corn plants from a corn field between 50 days and 80 days after fertilization or silking of the plurality of corn plants. In an aspect, a method provided herein comprises harvesting a plurality of corn plants from a corn field between 50 days and 70 days after fertilization or silking of the plurality of corn plants. In an aspect, a method provided herein comprises harvesting a plurality of corn plants from a corn field between 60 days and 120 days after fertilization or silking of the plurality of corn plants. In an aspect, a method provided herein comprises harvesting a plurality of corn plants from a corn field between 60 days and 90 days after fertilization or silking of the plurality of corn plants.

In an aspect, a method provided herein comprises harvesting a plurality of corn plants from a corn field at least 30 days after fertilization or silking of at least 50%, at least 60%, at least 70%, at least 80%, at least 90%, or 100% of the plurality of corn plants. In an aspect, a method provided herein comprises harvesting a plurality of corn plants from a corn field at least 35 days after fertilization or silking of at least 50%, at least 60%, at least 70%, at least 80%, at least 90%, or 100% of the plurality of corn plants. In an aspect, a method provided herein comprises harvesting a plurality of corn plants from a corn field at least 40 days after fertilization or silking of at least 50%, at least 60%, at least 70%, at least 80%, at least 90%, or 100% of the plurality of corn plants. In an aspect, a method provided herein comprises harvesting a plurality of corn plants from a corn field at least 45 days after fertilization or silking of at least 50%, at least 60%, at least 70%, at least 80%, at least 90%, or 100% of the plurality of corn plants. In an aspect, a method provided herein comprises harvesting a plurality of corn plants from a corn field at least 50 days after fertilization or silking of at least 50%, at least 60%, at least 70%, at least 80%, at least 90%, or 100% of the plurality of corn plants. In an aspect, a method provided herein comprises harvesting a plurality of corn plants from a corn field at least 55 days after fertilization or silking of at least 50%, at least 60%, at least 70%, at least 80%, at least 90%, or 100% of the plurality of corn plants. In an aspect, a method provided herein comprises harvesting a plurality of corn plants from a corn field at least 60 days after fertilization or silking of at least 50%, at least 60%, at least 70%, at least 80%, at least 90%, or 100% of the plurality of corn plants. In an aspect, a method provided herein comprises harvesting a plurality of corn plants from a corn field at least 65 days after fertilization or silking of at least 50%, at least 60%, at least 70%, at least 80%, at least 90%, or 100% of the plurality of corn plants. In an aspect, a method provided herein comprises harvesting a plurality of corn plants from a corn field at least 70 days after fertilization or silking of at least 50%, at least 60%, at least 70%, at least 80%, at least 90%, or 100% of the plurality of corn plants. In an aspect, a method provided herein comprises harvesting a plurality of corn plants from a corn field at least 75 days after fertilization or silking of at least 50%, at least 60%, at least 70%, at least 80%, at least 90%, or 100% of the plurality of corn plants. In an aspect, a method provided herein comprises harvesting a plurality of corn plants from a corn field at least 80 days after fertilization or silking of at least 50%, at least 60%, at least 70%, at least 80%, at least 90%, or 100% of the plurality of corn plants. In an aspect, a method provided herein comprises harvesting a plurality of corn plants from a corn field at least 85 days after fertilization or silking of at least 50%, at least 60%, at least 70%, at least 80%, at least 90%, or 100% of the plurality of corn plants. In an aspect, a method provided herein comprises harvesting a plurality of corn plants from a corn field at least 90 days after fertilization or silking of at least 50%, at least 60%, at least 70%, at least 80%, at least 90%, or 100% of the plurality of corn plants. In an aspect, a method provided herein comprises harvesting a plurality of corn plants from a corn field at least 120 days after fertilization or silking of at least 50%, at least 60%, at least 70%, at least 80%, at least 90%, or 100% of the plurality of corn plants.

In an aspect, a method provided herein comprises harvesting a plurality of corn plants from a corn field between 50 days and 120 days after fertilization or silking of at least 50%, at least 60%, at least 70%, at least 80%, at least 90%, or 100% of the plurality of corn plants. In an aspect, a method provided herein comprises harvesting a plurality of corn plants from a corn field between 50 days and 90 days after fertilization or silking of at least 50%, at least 60%, at least 70%, at least 80%, at least 90%, or 100% of the plurality of corn plants. In an aspect, a method provided herein comprises harvesting a plurality of corn plants from a corn field between 50 days and 80 days after fertilization or silking of at least 50%, at least 60%, at least 70%, at least 80%, at least 90%, or 100% of the plurality of corn plants. In an aspect, a method provided herein comprises harvesting a plurality of corn plants from a corn field between 50 days and 70 days after fertilization or silking of at least 50%, at least 60%, at least 70%, at least 80%, at least 90%, or 100% of the plurality of corn plants. In an aspect, a method provided herein comprises harvesting a plurality of corn plants from a corn field between 60 days and 120 days after fertilization or silking of at least 50%, at least 60%, at least 70%, at least 80%, at least 90%, or 100% of the plurality of corn plants. In an aspect, a method provided herein comprises harvesting a plurality of corn plants from a corn field between 60 days and 90 days after fertilization or silking of at least 50%, at least 60%, at least 70%, at least 80%, at least 90%, or 100% of the plurality of corn plants.

The following are non-limiting exemplary embodiments of the present disclosure:

1. A method comprising harvesting a plurality of corn plants from a field at least 50 days after fertilization or silking of at least 50% of said plurality of corn plants, wherein fewer than or equal to 50% of said corn plants have lodged at the time of harvest.
2. A method comprising harvesting a plurality of corn plants from a field at least 50 days after at least 50% of said corn plants have reached R3 stage, wherein fewer than or equal to 50% of said corn plants have lodged at the time of harvest.
3. A method comprising harvesting a plurality of corn plants from a field at least 50 days after fertilization or silking of at least 50% of said plurality of corn plants, wherein the average kernel moisture content is less than or equal to 30% or the kernel moisture content of a corn plant of the plurality of corn plants is less than or equal to 30%, and wherein fewer than or equal to 50% of said corn plants have lodged at the time of harvest.
4. A method comprising harvesting a plurality of corn plants from a field at least 50 days after at least 50% of said corn plants have reached R3 stage, wherein average kernel moisture content is less than or equal to 30% or the kernel moisture content of a corn plant of the plurality of corn plants is less than or equal to 30%, and wherein fewer than or equal to 50% of said corn plants have lodged at the time of harvest.
5. A method comprising harvesting a plurality of corn plants from a field at least 50 days after at fertilization or silking of at least 50% of said plurality of corn plants, wherein the average yield of said field is at least 170 bushels per acre, and wherein fewer than or equal to 50% of said corn plants have lodged at the time of harvest.
6. A method comprising harvesting a plurality of corn plants from a field at least 50 days after at least 50% of said corn plants have reached R3 stage, wherein the average yield of said field is at least 170 bushels per acre, and wherein fewer than or equal to 50% of said corn plants have lodged at the time of harvest.
7. A method comprising harvesting a plurality of corn plants from a field at least 1 day after the average kernel moisture content of at least 50% of said plurality of corn plants is between 10% and 30% or the kernel moisture content of a corn plant of the plurality of corn plants is between 10% and 30%, wherein fewer than or equal to 50% of said corn plants have lodged at the time of harvest.
8. The method of any one of embodiments 1, 3, 5 or 7, wherein said harvesting is performed at least 55 days after said fertilization or silking.
9. The method of any one of embodiments 1, 3, 5 or 7, wherein said harvesting is performed at least 60 days after said fertilization or silking.
10. The method of any one of embodiments 1, 3, 5 or 7, wherein said harvesting is performed at least 75 days after said fertilization or silking.
11. The method of any one of embodiments 1, 3, 5 or 7, wherein said harvesting is performed at least 90 days after said fertilization or silking.
12. The method of any one of embodiments 1, 3, 5 or 7, wherein said harvesting is performed at least 120 days after said fertilization or silking.
13. The method of any one of embodiments 1, 3, 5 or 7, wherein said harvesting is performed between 50 days and 90 days after said fertilization or silking.
14. The method of any one of embodiments 1, 3, 5 or 7, wherein said harvesting is performed between 50 days and 80 days after said fertilization or silking.
15. The method of any one of embodiments 1, 3, 5 or 7, wherein said harvesting is performed between 50 days and 70 days after said fertilization or silking.
16. The method of any one of embodiments 1, 3, 5 or 7, wherein said harvesting is performed between 60 days and 90 days after said fertilization or silking.
17. The method of any one of embodiments 1, 3, 5 or 7, wherein said harvesting is performed between 60 days and 120 days after said fertilization or silking.
18. The method of any one of embodiments 2, 4, or 6, wherein said harvesting is performed at least 55 days after at least 50% of said corn plants have reached R3 stage.
19. The method of any one of embodiments 2, 4, or 6, wherein said harvesting is performed at least 60 days after at least 50% of said corn plants have reached R3 stage.
20. The method of any one of embodiments 2, 4, or 6, wherein said harvesting is performed at least 75 days after at least 50% of said corn plants have reached R3 stage.
21. The method of any one of embodiments 2, 4, or 6, wherein said harvesting is performed at least 90 days after at least 50% of said corn plants have reached R3 stage.
22. The method of any one of embodiments 2, 4, or 6, wherein said harvesting is performed at least 120 days after at least 50% of said corn plants have reached R3 stage.
23. The method of any one of embodiments 2, 4, or 6, wherein said harvesting is performed between 50 days and 90 days after at least 50% of said corn plants have reached R3 stage.
24. The method of any one of embodiments 2, 4, or 6, wherein said harvesting is performed between 50 days and 80 days after at least 50% of said corn plants have reached R3 stage.
25. The method of any one of embodiments 2, 4, or 6, wherein said harvesting is performed between 50 days and 70 days after at least 50% of said corn plants have reached R3 stage.
26. The method of any one of embodiments 2, 4, or 6, wherein said harvesting is performed between 60 days and 90 days after at least 50% of said corn plants have reached R3 stage.
27. The method of any one of embodiments 2, 4, or 6, wherein said harvesting is performed between 60 days and 120 days after at least 50% of said corn plants have reached R3 stage.
28. The method of any one of embodiments 1-7, wherein fewer than or equal to 40% of said corn plants have lodged at the time of harvest.
29. The method of any one of embodiments 1-7, wherein fewer than or equal to 30% of said corn plants have lodged at the time of harvest.
30. The method of any one of embodiments 1-7, wherein fewer than or equal to 20% of said corn plants have lodged at the time of harvest.
31. The method of any one of embodiments 1-7, wherein fewer than or equal to 10% of said corn plants have lodged at the time of harvest.
32. The method of any one of embodiments 1-7, wherein between 0% and 50% of said corn plants have lodged at the time of harvest.
33. The method of any one of embodiments 1-7, wherein between 10% and 50% of said corn plants have lodged at the time of harvest.
34. The method of any one of embodiments 1-7, wherein between 20% and 40% of said corn plants have lodged at the time of harvest.
35. The method of any one of embodiments 1-6, wherein between 0% and 30% of said corn plants have lodged at the time of harvest.
36. The method of any one of embodiments 1-7, wherein between 0% and 20% of said corn plants have lodged at the time of harvest.
37. The method of any one of embodiments 1-7, wherein between 0% and 10% of said corn plants have lodged at the time of harvest.
38. The method of any one of embodiments 1-7, wherein the average height of said corn plants is less than or equal to 1.8 meters at the time of harvest.
39. The method of any one of embodiments 1-7, wherein the average height of said corn plants is less than or equal to 1.7 meters at the time of harvest.
40. The method of any one of embodiments 1-7, wherein the average height of said corn plants is less than or equal to 1.6 meters at the time of harvest.

41. The method of any one of embodiments 1-7, wherein the average height of said corn plants is less than or equal to 1.5 meters at the time of harvest.
42. The method of any one of embodiments 1-7, wherein the average height of said corn plants is between 1.5 meters and 1.7 meters at the time of harvest.
43. The method of any one of embodiments 37-40, wherein said height is measured as the distance between the soil and the ligule or collar of the uppermost fully-expanded leaf.
44. The method of any one of embodiments 37-40, wherein said height is measured as the distance between the soil and the upper leaf surface of the leaf farthest from the soil.
45. The method of any one of embodiments 1-7, wherein at least 50% of said corn plants are inbred corn plants.
46. The method of any one of embodiments 1-7, wherein at least 50% of said corn plants are hybrid corn plants.
47. The method of any one of embodiments 1-7, wherein at least 50% of said corn plants are semi-dwarf corn plants.
48. The method of any one of embodiments 1-7, wherein at least 50% of said corn plants are dwarf corn plants.
49. The method of any one of embodiments 1-7, wherein at least 50% of said corn plants are brachytic corn plants.
50. The method of any one of embodiments 1-7, wherein at least 50% of said corn plants comprise a mutation in a br2 locus as compared to a wildtype br2 locus.
51. The method of any one of embodiments 1-7, wherein at least 50% of said corn plants comprise a heterologous polynucleotide capable of suppressing expression of a br2 gene or an mRNA transcribed therefrom.
52. The method of any one of embodiments 1-7, wherein at least 50% of said corn plants comprise a mutation in a GA20 oxidase locus as compared to a wildtype GA20 oxidase locus.
53. The method of any one of embodiments 1-7, wherein at least 50% of said corn plants comprise a heterologous polynucleotide capable of suppressing expression of a GA20 oxidase gene or an mRNA transcribed therefrom.
54. The method of any one of embodiments 1-7, wherein at least 50% of said corn plants comprise a mutation in a GA3 oxidase locus as compared to a wildtype GA3 oxidase locus.
55. The method of any one of embodiments 1-7, wherein at least 50% of said corn plants comprise a heterologous polynucleotide capable of suppressing expression of a GA3 oxidase gene or an mRNA transcribed therefrom.
56. The method of any one of embodiments 1-7, wherein said field comprises a planting density of at least 10,000 corn plants per acre.
57. The method of any one of embodiments 1-7, wherein said field comprises a planting density of between 10,000 corn plants per acre and 50,000 corn plants per acre.
58. The method of any one of embodiments 1-7, wherein the average yield of said field is at least 180 bushels per acre.
59. The method of any one of embodiments 1-7, wherein the average yield of said field is at least 190 bushels per acre.
60. The method of any one of embodiments 1-7, wherein the average yield of said field is at least 200 bushels per acre.
61. The method of any one of embodiments 1-7, wherein the average yield of said field is at least 210 bushels per acre.
62. The method of any one of embodiments 1-7, wherein the average yield of said field is at least 220 bushels per acre.
63. The method of any one of embodiments 1-7, wherein the average yield of said field is at least 250 bushels per acre.
64. The method of any one of embodiments 1-7, wherein the average yield of said field is between 160 bushels per acre and 260 bushels per acre.
65. The method of any one of embodiments 1-7, wherein the average yield of said field is between 180 bushels per acre and 260 bushels per acre.
66. The method of any one of embodiments 1-7, wherein the average yield of said field is between 200 bushels per acre and 260 bushels per acre.
67. The method of any one of embodiments 1-7, wherein the average kernel moisture content is equal to or less than 29% or the kernel moisture content of a corn plant of the plurality of corn plants is less than or equal to 29%.
68. The method of any one of embodiments 1-7, wherein the average kernel moisture content is equal to or less than 28% or the kernel moisture content of a corn plant of the plurality of corn plants is less than or equal to 28%.
69. The method of any one of embodiments 1-7, wherein the average kernel moisture content is equal to or less than 27% or the kernel moisture content of a corn plant of the plurality of corn plants is less than or equal to 27%.
70. The method of any one of embodiments 1-7, wherein the average kernel moisture content is equal to or less than 26% or the kernel moisture content of a corn plant of the plurality of corn plants is less than or equal to 26%.
71. The method of any one of embodiments 1-7, wherein the average kernel moisture content is equal to or less than 25% or the kernel moisture content of a corn plant of the plurality of corn plants is less than or equal to 25%.
72. The method of any one of embodiments 1-7, wherein the average kernel moisture content is equal to or less than 24% or the kernel moisture content of a corn plant of the plurality of corn plants is less than or equal to 24%.
73. The method of any one of embodiments 1-7, wherein the average kernel moisture content is equal to or less than 23% or the kernel moisture content of a corn plant of the plurality of corn plants is less than or equal to 23%.
74. The method of any one of embodiments 1-7, wherein the average kernel moisture content is equal to or less than 22% or the kernel moisture content of a corn plant of the plurality of corn plants is less than or equal to 22%.
75. The method of any one of embodiments 1-7, wherein the average kernel moisture content is equal to or less than 21% or the kernel moisture content of a corn plant of the plurality of corn plants is less than or equal to 21%.
76. The method of any one of embodiments 1-7, wherein the average kernel moisture content is equal to or less than 20% or the kernel moisture content of a corn plant of the plurality of corn plants is less than or equal to 20%.
77. The method of any one of embodiments 1-7, wherein the average kernel moisture content is equal to or less than 19% or the kernel moisture content of a corn plant of the plurality of corn plants is less than or equal to 19%.
78. The method of any one of embodiments 1-7, wherein the average kernel moisture content is equal to or less than 18% or the kernel moisture content of a corn plant of the plurality of corn plants is less than or equal to 18%.
79. The method of any one of embodiments 1-7, wherein the average kernel moisture content is equal to or less than 17% or the kernel moisture content of a corn plant of the plurality of corn plants is less than or equal to 17%.
80. The method of any one of embodiments 1-7, wherein the average kernel moisture content is equal to or less than 16% or the kernel moisture content of a corn plant of the plurality of corn plants is less than or equal to 16%.
81. The method of any one of embodiments 1-7, wherein the average kernel moisture content is equal to or less than 15% or the kernel moisture content of a corn plant of the plurality of corn plants is less than or equal to 15%.
82. The method of any one of embodiments 1-7, wherein the average kernel moisture content is between 15% and 30% or the kernel moisture content of a corn plant of the plurality of corn plants is between 15% and 30%.
83. The method of any one of embodiments 1-7, wherein the average kernel moisture content is between 10% and 25% or the kernel moisture content of a corn plant of the plurality of corn plants is between 10% and 25%.
84. The method of any one of embodiments 1-7, wherein the average kernel moisture content is between 15% and 25% or the kernel moisture content of a corn plant of the plurality of corn plants is between 15% and 25%.
85. The method of any one of embodiments 1-7, wherein the average kernel moisture content is between 10% and 20% or the kernel moisture content of a corn plant of the plurality of corn plants is between 10% and 20%.
86. The method of any one of embodiments 1-7, wherein the average kernel moisture content is between 20% and 30% or the kernel moisture content of a corn plant of the plurality of corn plants is between 20% and 30%.
87. The method of embodiment 7, wherein said harvesting occurs at least 2 days, at least 3 days, at least 4 days, at least 5 days, at least 7 days, at least 10 days, at least 15 days, at least 20 days, at least 25 days, at least 30 days, at least 35 days, at least 40 days, at least 45 days, at least 50 days, at least 55 days, at least 60 days, at least 65 days, or at least 70 days after the average kernel moisture content of said plurality of corn plants is between 10% and 30%, or after the kernel moisture content of a corn plant of said plurality of corn plants is between 10% and 30%.
88. The method of any one of embodiments 1-7, wherein said method comprises growing said plurality of said corn plants in said corn field prior to said harvesting.

EXAMPLES

Example 1: Semi-Dwarf Corn Improves Stalk Health for Late Season Harvest

Three semi-dwarf (SD) and three wild-type control hybrids were planted in 30 inch rows with a density of approximately 42,000 plants per acre in two separate locations. When hybrids reached full maturity, Stalk Lodging Percent (STLP) and Stalk Health Good Pith Percentage (SHGPP) were collected at two separate locations at normal (October 10$^{th}$) and late (November 12$^{th}$) harvest dates. Hybrids were replicated twelve times for each harvest date. Hybrids harvested at normal harvest date had a moisture content of approximately 25%. At late harvest date, hybrids had a moisture content of approximately 15%. STLP was collected by counting the number of lodged plants by the total number of plants per plot at normal harvest and at late harvest prior to combine harvest. After combine harvest, SHGPP was collected cutting the residual stalks between first and second node then observing the intactness of the pith. Percentage of intactness was designated for each stalk. As shown in Table 1, SD hybrids have improved stalk health as compared to WT hybrids.

TABLE 1

Stalk Health of SD versus WT Control Hybrids at Normal and Delayed Harvest

| Stature | Line | SHGPP | | STLP | |
| --- | --- | --- | --- | --- | --- |
| | | Normal Harvest | Late Harvest | Normal Harvest | Late Harvest |
| SD | Line #1 | 59.3 | 62.1 | 0.6 | 1.1 |
| | Line #2 | 70.3 | 52.6 | 2.1 | 3.5 |
| | Line #3 | 62.0 | 53.5 | 1.9 | 2.2 |
| | Semi-Dwarf Total | 63.8 | 56.1 | 1.5 | 2.2 |
| WT | Line #4 | 43.5 | 29.4 | 1.5 | 3.4 |
| | Line #5 | 23.9 | 18.1 | 2.6 | 5.5 |
| | Line #6 | 51.8 | 49.1 | 0.5 | 8.6 |
| | WT Total | 39.7 | 32.3 | 1.5 | 5.9 |

In this example, SD hybrids overall improved stalk health good pith percent as compared to WT at normal harvest, 63.8 versus 39.7 percent, respectively. This improved stalk health good pith percent was observed at late harvest, 56.1 for SD hybrids compared to 32.3 for WT hybrids (FIG. 1). At late harvest, the SD hybrids significantly reduced stalk lodging as compared to WT, 2.2 versus 5.9, respectively. This experiment demonstrates that SD hybrids allow growers flexibility in harvest by extending the window of time to harvest due to improved stalk health and standability.

Example 2: Planting Date and Corn Maturity Impacts Harvest Window

Each growing season farmers must balance planting the corn crop after the threat of freezing temperatures has passed, yet with enough time to allow maximum growing degree days (GDDs) for crop development to maturity and dry down before the first frost. Corn GDDs are calculated by subtracting the plant's lower base or threshold temperature of 50° F. (10° C.) from the average daily air temperature in ° F. or ° C. Average daily air temperature is calculated by averaging the daily maximum and minimum air temperatures measured in any 24-hour period. To fully mature corn, a certain amount of accumulated GDDs are required in relation to its relative maturity (RM) and geographical location. In the northern hemisphere, including the North American continent, the corn planting window is typically within the months of April, May and June (see, e.g., FIG. 2). Emergence, growth, and pollination of the crop follows through stages of silking, dough, dent, maturity (black layer), and grain harvest (see, e.g., FIG. 2). When corn reaches physiological maturity (black layer), it is around 30% moisture. Additionally, late-planted and full-season corn products tend to dry more slowly. In general, it takes about 30 GDDs per point of moisture to dry corn from maturity to 25% moisture content (see, e.g., Table 2). After reaching maturity, typical drying rates may range from 0.4% to 0.8% loss of moisture content per day (see, e.g., Table 2).

The optimum harvest moisture content for corn is approximately 23% to 25%. At this moisture level, kernels shell easily and stalks generally stand better, which can make harvesting more efficient. A normal harvest loss level of a timely and efficient harvest can be 1% to 2%. Knowing the grain moisture content at maturity can help predict grain moisture at different potential harvest dates. A year with wet weather and delays in planting may result in slower field drying of corn. However, if enough GDDs accumulate, the drying process may be hastened. Other factors may also come into play if harvest is delayed. For example, corn could have developed a shallow root system because of the early-season moisture. In addition, conditions may have been conducive for the development of stalk rots and stalk cannibalization in corn. These factors could lead to higher than normal harvest losses because of an increased risk for stalk lodging in corn at maturity. Delaying harvest until corn of GDD accumulation to reach 25% grain moisture for harvest, or 15 to 16 days of GDD accumulation to reach 20% grain moisture for harvest (assuming optimal weather conditions). As described herein, at minimum an additional 30 GDDs per point of grain moisture content to reach 25% or less would be required beyond the maturity date.

Figure 2:
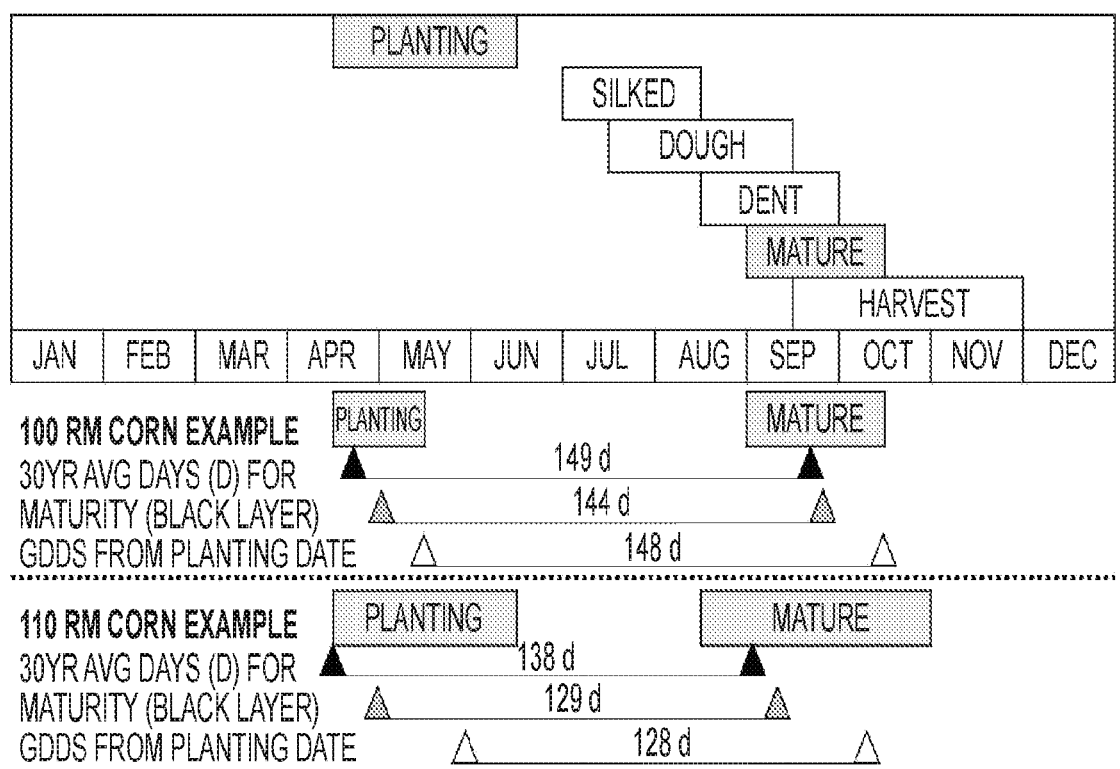
FIG. 2 depicts an example of a planting, maturation, and harvesting schedule for corn.

In the northern hemisphere, or on the North America continent, the corn harvest window is typically within the months of September and November (see, e.g., FIG. 2). The longer the amount of time from crop maturity to harvest the greater the risk of increased harvest losses unless the corn variety can provide a benefit of improved standability (less susceptible to lodging), such as the semi-dwarf (SD) corn in Example 1. Stated another way, semi-dwarf or shorter stature corn varieties or lines with improved standability that are less susceptible to lodging (such as the disclosed SD corn) provide a benefit to farmers or crop growers by enabling grain dry down in the field for a duration of time beyond standard expectations from conventional corn varieties. For example, a farmer would have an increased probability to reach 20% grain moisture prior to harvest, ranging from an extra 8 to 10 days at minimum (beyond 25% grain moisture) for the crop to remain in the field in the example provided (see, e.g., Table 2).

TABLE 2

| Location | Year(s) | RM | Total GDD to Maturity | Planting Date | Maturity (Black Layer) | Days to reach Total GDD | Average GDD per day | See Moisture at Maturity | Days to reach 25% Moisture | Harvest Date 25% Moisture | Days to reach 20% Moisture | Harvest Date 20% Moisture |
|---|---|---|---|---|---|---|---|---|---|---|---|---|
| MN | 1981-2010 | 100 | 2401 | Apr 20th | Sep 16th | 149 | 16 | 30% | 9 | Sep 25th | 19 | Oct 4th |
| MN | 1981-2010 | 100 | 2401 | May 1st | Sep 22nd | 144 | 17 | 30% | 9 | Sep 30th | 18 | Oct 9th |
| MN | 1981-2010 | 100 | 2401 | May 20th | Oct 15th | 148 | 16 | 30% | 9 | Oct 24th | 18 | Nov 2nd |
| IL | 1981-2010 | 110 | 2642 | Apr 15th | Aug 31st | 138 | 19 | 30% | 8 | Sep 7th | 16 | Sep 15th |
| IL | 1981-2010 | 110 | 2642 | May 1st | Sep 7th | 129 | 20 | 30% | 7 | Sep 14th | 15 | Sep 21st |
| IL | 1981-2010 | 110 | 2642 | Jun 1st | Oct 7th | 128 | 21 | 30% | 7 | Oct 14th | 15 | Oct 21st | dries down to 17% to 19% moisture content can save on artificial drying costs. However, as corn dries down in the field there is greater potential for excess harvest losses from stalk lodging, in part due to normal senescence of the plant through the maturation process. Most harvest losses are mechanical, caused by corn grain never getting into the combine harvester because it cannot be collected from lodged plants on the ground. Allowing corn to dry down in the field could lead to excess harvest losses, as much as 2% to 10% or more above the normal level from a timely and efficient harvest.

Corn plants that are less susceptible to lodging that have improved stalk health for late season harvest reduce the risk of harvest losses (see Example 1). Farmers make planting decisions of corn hybrids based on their geographical region and historical weather data for spring and fall frosts. In one example, a farmer in Minnesota, USA (MN) planting a 100 RM corn hybrid can expect between 144 days and 149 days to accumulate enough GDDs for crop maturity depending on the planting date based on a 30 year average (1981-2010). The same farmer would need an additional 9 days of GDD accumulation to reach 25% grain moisture for harvest, or 18 to 19 days of GDD accumulation to reach 20% grain moisture for harvest (assuming optimal weather conditions). In another example, a farmer in Illinois, USA (IL) planting a 110 RM corn hybrid can expect between 128 days and 138 days to accumulate enough GDDs for crop maturity depending on the planting date based on a 30 year average (1981-2010). The same farmer would need an additional 7 to 8 days

The invention claimed is:

1. A method of late season harvesting corn, wherein the method comprises late-season harvesting seed from a plurality of corn plants from a field, wherein late-season harvesting comprises harvesting at least 100 days after fertilization or silking of at least 80% of said plurality of corn plants, wherein the kernel moisture content of each corn plant of said plurality of corn plants is between 10% and 15%, wherein the average yield of said field is at least 210 bushels per acre, wherein fewer than or equal to 3.5% of said corn plants have lodged at the time of harvest, and wherein said plurality of corn plants are semi-dwarf and comprise a mutation in the brachytic2 (br2) locus as compared to the wildtype br2 locus.

2. The method of claim 1, wherein the plurality of corn plants from the field are harvested at least 50 days after at least 80% of said corn plants have reached R3 stage.

3. The method of claim 1, wherein fewer than or equal to 1% of said corn plants have lodged at the time of harvest.

4. The method of claim 1, wherein the average height of said corn plants is less than or equal to 1.7 meters at the time of harvest.

5. The method of claim 4, wherein said height is measured as the distance between the soil and the ligule of the uppermost fully-expanded leaf.

6. The method of claim 1, wherein at least 50% of said corn plants are inbred corn plants.

7. The method of claim 1, wherein at least 50% of said corn plants are hybrid corn plants.

8. The method of claim 1, wherein said field comprises a planting density of at least 10,000 corn plants per acre.

9. The method of claim 1, wherein said method comprises growing said plurality of said corn plants in said corn field prior to said harvesting.

10. The method of claim 1, wherein said harvesting is performed at least 110 days after said fertilization or silking.

11. The method of claim 1, wherein the plurality of corn plants from the field are harvested at least 60 days after at least 80% of said corn plants have reached R3 stage.

12. The method of claim 1, wherein the plurality of corn plants from the field are harvested at least 70 days after at least 80% of said corn plants have reached R3 stage.

13. The method of claim 1, wherein the plurality of corn plants from the field are harvested at least 80 days after at least 80% of said corn plants have reached R3 stage.

14. The method of claim 1, wherein the plurality of corn plants from the field are harvested at least 90 days after at least 80% of said corn plants have reached R3 stage.

15. The method of claim 1, wherein said harvesting is performed at least 10 days after the average kernel moisture content of said plurality of corn plants is less than 30%.

16. The method of claim 1, wherein said harvesting is performed at least 10 days after the average kernel moisture content of said plurality of corn plants is less than 25%.

17. The method of claim 1, wherein said harvesting is performed at least 10 days after the average kernel moisture content of said plurality of corn plants is less than 20%.

18. The method of claim 1, wherein said harvesting is performed at least 10 days after the average kernel moisture content of said plurality of corn plants is less than 15%.

19. The method of claim 1, wherein said harvesting is performed at least 20 days after the average kernel moisture content of said plurality of corn plants is less than 30%.

20. The method of claim 1, wherein said harvesting is performed at least 20 days after the average kernel moisture content of said plurality of corn plants is less than 25%.

21. The method of claim 1, wherein said harvesting is performed at least 20 days after the average kernel moisture content of said plurality of corn plants is less than 20%.

22. The method of claim 1, wherein said harvesting is performed at least 20 days after the average kernel moisture content of said plurality of corn plants is less than 15%.

23. A method of late season harvesting corn, wherein the method comprises
late-season harvesting seed from a plurality of corn plants from a field, wherein late-season harvesting comprises harvesting at least 100 days after fertilization or silking of at least 80% of said plurality of corn plants,
wherein the kernel moisture content of each corn plant of said plurality of corn plants is between 10% and 15%,
wherein the average yield of said field is at least 210 bushels per acre,
wherein fewer than or equal to 3.5% of said corn plants have lodged at the time of harvest, and
wherein said plurality of corn plants are semi-dwarf and comprise a heterologous polynucleotide that suppresses expression of the brachytic2 gene or an mRNA transcribed therefrom.

24. The method of claim 23, wherein the plurality of corn plants from the field are harvested at least 50 days after at least 80% of said corn plants have reached R3 stage.

25. The method of claim 23, wherein fewer than or equal to 1% of said corn plants have lodged at the time of harvest.

26. The method of claim 23, wherein said harvesting is performed at least 110 days after said fertilization or silking.

27. The method of claim 23, wherein the plurality of corn plants from the field are harvested at least 60 days after at least 80% of said corn plants have reached R3 stage.

28. The method of claim 23, wherein the plurality of corn plants from the field are harvested at least 70 days after at least 80% of said corn plants have reached R3 stage.

29. The method of claim 23, wherein the plurality of corn plants from the field are harvested at least 80 days after at least 80% of said corn plants have reached R3 stage.

30. The method of claim 23, wherein the plurality of corn plants from the field are harvested at least 90 days after at least 80% of said corn plants have reached R3 stage.

31. The method of claim 23, wherein said harvesting is performed at least 10 days after the average kernel moisture content of said plurality of corn plants is less than 30%.

32. The method of claim 23, wherein said harvesting is performed at least 10 days after the average kernel moisture content of said plurality of corn plants is less than 25%.

33. The method of claim 23, wherein said harvesting is performed at least 10 days after the average kernel moisture content of said plurality of corn plants is less than 20%.

34. The method of claim 23, wherein said harvesting is performed at least 10 days after the average kernel moisture content of said plurality of corn plants is less than 15%.

35. The method of claim 23, wherein said harvesting is performed at least 20 days after the average kernel moisture content of said plurality of corn plants is less than 30%.

36. The method of claim 23, wherein said harvesting is performed at least 20 days after the average kernel moisture content of said plurality of corn plants is less than 25%.

37. The method of claim 23, wherein said harvesting is performed at least 20 days after the average kernel moisture content of said plurality of corn plants is less than 20%.

38. The method of claim 23, wherein said harvesting is performed at least 20 days after the average kernel moisture content of said plurality of corn plants is less than 15%.

* * * * *

UNITED STATES PATENT AND TRADEMARK OFFICE
CERTIFICATE OF CORRECTION

PATENT NO. : 12,274,205 B2
APPLICATION NO. : 17/298979
DATED : April 15, 2025
INVENTOR(S) : Ty J. Barten, Bryce Lemke and Edward James Cargill Page 1 of 1

It is certified that error appears in the above-identified patent and that said Letters Patent is hereby corrected as shown below:

On the Title Page

Under Related U.S. Application Data found at Item (60), delete "Provisional application No. 62/886,761, filed on Aug. 14, 2019, provisional application No. 62/778,368, filed on Dec. 12, 2018" and insert --Provisional application No. 62/886,761, filed on Aug. 14, 2019, provisional application No. 62/775,368, filed on Dec. 4, 2018--

Signed and Sealed this
Twenty-seventh Day of May, 2025

Coke Morgan Stewart
*Acting Director of the United States Patent and Trademark Office*